(12) United States Patent
Nishino et al.

(10) Patent No.: US 8,600,127 B2
(45) Date of Patent: Dec. 3, 2013

(54) RADIATION IMAGE CAPTURING SYSTEM, RADIATION DETECTING APPARATUS, IMAGE CAPTURING BASE, RADIATION IMAGE CAPTURING METHOD, AND PROGRAM

(75) Inventors: Naoyuki Nishino, Minami-ashigara (JP); Yasunori Ohta, Yokohama (JP); Naoki Mochizuki, Minami-ashigara (JP); Daiki Harada, Minami-ashigara (JP); Hiroshi Fukuda, Tokyo (JP); Eiichi Kito, Minami-ashigara (JP); Keiji Tsubota, Minami-ashigara (JP); Yutaka Yoshida, Fuchu (JP); Takeshi Kamiya, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 1314 days.

(21) Appl. No.: 12/393,865

(22) Filed: Feb. 26, 2009

(65) Prior Publication Data
US 2009/0220049 A1    Sep. 3, 2009

(30) Foreign Application Priority Data

Feb. 29, 2008  (JP) ................................. 2008-051170
Aug. 19, 2008  (JP) ................................. 2008-210696
Feb. 16, 2009  (JP) ................................. 2009-032743

(51) Int. Cl.
*G06K 9/00* (2006.01)
(52) U.S. Cl.
USPC .......................................................... 382/128
(58) Field of Classification Search
USPC ................................................ 382/128–134
See application file for complete search history.

(56) References Cited

U.S. PATENT DOCUMENTS

| 6,205,347 | B1 * | 3/2001 | Morgan et al. ................. 600/407 |
| 7,167,541 | B2 | 1/2007 | Kaito |
| 2002/0081007 | A1 * | 6/2002 | Arakawa ........................ 382/130 |
| 2004/0170310 | A1 * | 9/2004 | Kurahashi ..................... 382/128 |
| 2006/0219926 | A1 | 10/2006 | Shoji et al. |

FOREIGN PATENT DOCUMENTS

| JP | 07-265286 A | 10/1995 |
| JP | 2000-105297 A | 4/2000 |
| JP | 3494683 B2 | 2/2004 |
| JP | 2004-144651 A | 5/2004 |
| JP | 2005-270201 A | 10/2005 |
| JP | 2006-247137 A | 9/2006 |

OTHER PUBLICATIONS

Communication, dated Jun. 6, 2012, issued in corresponding EP Application No. 09002750.9, 6 pages.

(Continued)

*Primary Examiner* — Alex Liew
(74) *Attorney, Agent, or Firm* — Sughrue Mion, PLLC

(57) ABSTRACT

A radiation image capturing system includes a first image capturing apparatus for capturing a radiation image of a subject, a second image capturing apparatus for capturing a radiation image of the subject, the second image capturing apparatus having a specification different from that of the first image capturing apparatus, an image correcting device for correcting the radiation image of the subject which is captured by the second image capturing apparatus such that the radiation image of the subject which is captured by the second image capturing apparatus has the same magnification as that of the radiation image of the subject which is captured by the first image capturing apparatus, and a display unit for displaying the corrected radiation image. The radiation images captured by the image capturing apparatus of different specifications are corrected to have the same magnification.

2 Claims, 20 Drawing Sheets

(56) References Cited

OTHER PUBLICATIONS

Armato et al., "Automated Registration of Frontal and Lateral Radionuclide Lung Scans with Digital Chest Radiographs," Academic Radiology, vol. 7, No. 1, Jul. 1, 2000, pp. 530-539, XP005307122.

Communication, dated Oct. 2, 2012, issued in corresponding EP Application No. 09002750.9, 9 pages.

Communication pursuant to Article 94(3) EPC, dated May 27, 2013, issued in corresponding EP Application No. 09 002 750.9, 5 pages.

\* cited by examiner

RADIATION IMAGE CAPTURING SYSTEM, RADIATION DETECTING APPARATUS, IMAGE CAPTURING BASE, RADIATION IMAGE CAPTURING METHOD, AND PROGRAM

BACKGROUND OF THE INVENTION

1.. Field of the Invention

The present invention relates to a radiation image capturing system, a radiation detecting apparatus, an image capturing base, a radiation image capturing method, and a program for correcting the magnifications of radiation images captured by a plurality of image capturing apparatus of different specifications.

2.. Description of the Related Art

In the medical field, there have widely been used radiation image capturing apparatus which apply a radiation to a subject and guide the radiation that has passed through the subject to a radiation detector, which captures a radiation image from the radiation.

One known radiation detector is a stimulable phosphor panel which stores a radiation energy representative of a radiation image in a phosphor. When the stimulable phosphor panel is irradiated with stimulating light, the phosphor emits stimulated light representative of the stored radiation image. The stimulable phosphor panel with the radiation image recorded therein is supplied to a reading apparatus which reads the stored radiation image as a visible radiation image.

In sites of medical practice such as operating rooms or the like, it is necessary to read recorded radiation image information immediately from a radiation detector for the purpose of quickly and appropriately treating the patient. As a radiation detector which meets such a requirement, there has been developed a radiation detector having a solid-state detector for converting a radiation directly into an electric signal or converting a radiation into visible light with a scintillator and then converting the visible light into an electric signal to read a detected radiation image.

There are available in the art various image capturing apparatus of different specifications for capturing radiation images using radiation detectors depending on the conditions of patients as subjects to be imaged and image capturing conditions including body regions to be imaged. Those different image capturing apparatus are controlled by respective processors having specifications corresponding to the specifications of the image capturing apparatus. According to a known radiographic system, various image capturing apparatus and processors are connected to a radiology information system (RIS) by an in-house network, and patient information and image capturing conditions set by the RIS which include image capturing methods, body regions to be imaged, radiation dose, etc. are supplied to the processors, which then control the corresponding image capturing apparatus to capture radiation images (see Japanese Laid-Open Patent Publication No. 2006-247137).

If a body region of interest of one patient is to be periodically imaged for follow-up observations, then it is necessary to capture radiation images of the body region with the same image capturing apparatus under the same image capturing conditions. However, the same image capturing apparatus may not be available when the patient has suffered certain status changes or when the image capturing apparatus is occupied. For example, when a patient is unable to walk, it is imaged by an image capturing apparatus while lying on the bed, and when the same patient is able to walk at a later time, it is imaged by another image capturing apparatus while in an upstanding posture. In this case, the radiation images of the patient are captured by the different image capturing apparatus. If the patient is spaced from the radiation detectors of the different image capturing apparatus by different distances or the radiation images captured by the different image capturing apparatus are processed by different image processing methods, then the radiation images may have different magnifications and hence may not be accurately compared with each other.

Various technologies have been used to process a radiation image of a subject, in relation to the subject according to the related art. Those technologies include an apparatus for processing a radiation image of a subject captured by an image capturing apparatus such that the generated radiation image has the same size as the subject (see Japanese Laid-Open Patent Publication No. 07-265286) and an apparatus for simultaneously capturing radiation images of a subject and a reference member of known dimensions and determining the dimensions and area of the subject from the radiation image of the reference member (see Japanese Laid-Open Patent Publication No. 2004-144651). Another known apparatus has an ordinary X-ray source for capturing ordinary radiation images and a microfocal X-ray source for capturing enlarged radiation images, which can selectively be used depending on a body region of interest of a subject for changing image magnifications (see Japanese Laid-Open Patent Publication No. 2005-270201).

The apparatus disclosed in Japanese Laid-Open Patent Publication No. 07-265286) displays the radiation image of the subject in full scale, but does not equalize the scales of radiation images captured by different image capturing apparatus. Though the apparatus disclosed in Japanese Laid-Open Patent Publication No. 2004-144651. can determine the dimensions of the subject, it does not equalize the scales of radiation images, either. The apparatus disclosed in Japanese Laid-Open Patent Publication No. 2005-270201. does not equalize the scales of radiation images captured by different image capturing apparatus as it only captures and displays radiation images at different magnifications depending on body regions of interest to be imaged.

SUMMARY OF THE INVENTION

It is an object of the present invention to provide a radiation image capturing system, a radiation image capturing method, and a program which are capable of displaying radiation images captured by a plurality of image capturing apparatus of different specifications at the same magnification.

Another object of the present invention to provide a radiation image capturing system, a radiation detecting apparatus, an image capturing base, a radiation image capturing method, and a program which are capable of equalizing the magnifications of image information captured using different image capturing bases.

According to a first aspect of the present invention, there is provided a radiation image capturing system comprising a first image capturing apparatus for capturing a radiation image of a subject, a second image capturing apparatus for capturing a radiation image of the subject, the second image capturing apparatus having a specification different from that of the first image capturing apparatus, an image correcting device for correcting the radiation image of the subject which is captured by the second image capturing apparatus such that the radiation image of the subject which is captured by the second image capturing apparatus has the same magnification as that of the radiation image of the subject which is captured by the first image capturing apparatus, and a display unit for displaying the corrected radiation image.

According to a second aspect of the present invention, there is also provided a method of capturing a radiation image with a radiation image capturing system including a first image capturing apparatus for capturing a radiation image of a subject, a second image capturing apparatus for capturing a radiation image of the subject, the second image capturing apparatus having specifications different from the first image capturing apparatus, and a display unit for displaying the radiation image, the method comprising the steps of acquiring a radiation image of the subject with the first image capturing apparatus, acquiring a radiation image of the subject with the second image capturing apparatus, correcting the radiation image of the subject which is captured by the second image capturing apparatus such that the radiation image of the subject which is captured by the second image capturing apparatus has the same magnification as that of the radiation image of the subject which is captured by the first image capturing apparatus, and displaying the corrected radiation image on the display unit.

According to a third aspect of the present invention, there is also provided a program for controlling a radiation image capturing system including a first image capturing apparatus for capturing a radiation image of a subject, a second image capturing apparatus for capturing a radiation image of the subject, the second image capturing apparatus having a specification different from that of the first image capturing apparatus, and a display unit for displaying the radiation image, to function as a unit for acquiring a radiation image of the subject with the first image capturing apparatus, a unit for acquiring a radiation image of the subject with the second image capturing apparatus, a unit for correcting the radiation image of the subject which is captured by the second image capturing apparatus such that the radiation image of the subject which is captured by the second image capturing apparatus has the same magnification as that of the radiation image of the subject which is captured by the first image capturing apparatus, and a unit for displaying the corrected radiation image on the display unit.

According to the first through third aspects of the present invention, the radiation images captured by the image capturing apparatus of different specifications are corrected to have the same magnification and displayed at the same magnification, so that the radiation images captured under different image capturing conditions can appropriately be evaluated by way of easy comparison.

According to a fourth aspect of the present invention, there is further provided a radiation image capturing system comprising an image capturing position information holding unit for holding image capturing position information with respect to a subject of a radiation detecting apparatus, disposed in an image capturing base, the radiation detecting apparatus detecting a radiation having passed through the subject and converting the detected radiation into radiation image information, an image capturing position information acquiring unit for acquiring the image capturing position information from the image capturing position information holding unit, and a magnification adjuster for adjusting an image magnification of the radiation image information based on the acquired image capturing position information.

According to a fifth aspect of the present invention, there is further provided a radiation detecting apparatus for detecting a radiation having passed through a subject and converting the detected radiation into radiation image information, comprising an image capturing position information holding unit for holding image capturing position information with respect to the subject of the radiation detecting apparatus disposed in an image capturing base, wherein an image magnification of the radiation image information is adjusted based on the image capturing position information.

According to a sixth aspect of the present invention, there is further provided an image capturing base housing therein a radiation detecting apparatus for detecting a radiation having passed through a subject and converting the detected radiation into radiation image information, comprising a loading detector for detecting when the radiation detecting apparatus is loaded, and an image capturing position information holding unit for holding image capturing position information of the loaded radiation detecting apparatus with respect to the subject, wherein an image magnification of the radiation image information is adjusted based on the image capturing position information.

According to a seventh aspect of the present invention, there is further provided a method of capturing a radiation image with a radiation image capturing system including a radiation detecting apparatus for detecting a radiation having passed through a subject and converting the detected radiation into radiation image information, an image capturing position information holding unit for holding image capturing position information of the radiation detecting apparatus with respect to the subject, and a display unit for displaying a radiation image based on the radiation image information, the method comprising the steps of acquiring the image capturing position information from the image capturing position information holding unit, adjusting an image magnification of the radiation image information based on the acquired image capturing position information, and displaying a radiation image based on the radiation image information with the adjusted image magnification, on the display unit.

According to an eighth aspect of the present invention, there is further provided a program for controlling a radiation image capturing system including a radiation detecting apparatus for detecting a radiation having passed through a subject and converting the detected radiation into radiation image information, and an image capturing position information holding unit for holding image capturing position information of the radiation detecting apparatus with respect to the subject, to function as a unit for acquiring the image capturing position information from the image capturing position information holding unit, a unit for adjusting an image magnification of the radiation image information based on the acquired image capturing position information, and a unit for displaying a radiation image based on the radiation image information with the adjusted image magnification.

According to the fourth through eighth aspects of the present invention, the magnifications of image information captured using different image capturing bases are equalized to each other based on the image capturing position information of the radiation detecting apparatus with respect to the subject. Therefore, the image information captured using the different image capturing bases can appropriately be evaluated by way of easy comparison.

The above and other objects, features, and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

Figure 1:
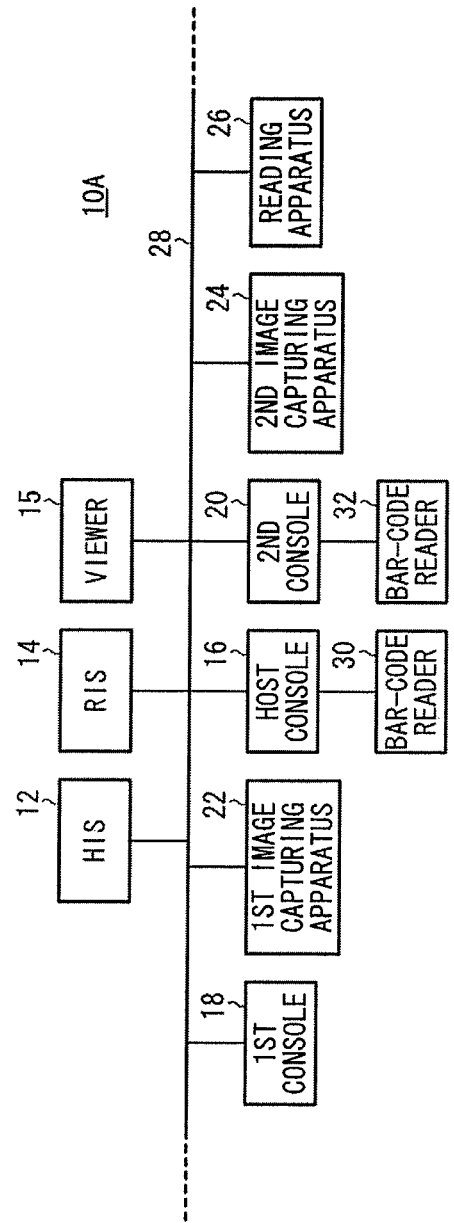
FIG. 1 is a block diagram of a first system according to the present invention.
Figure 2:
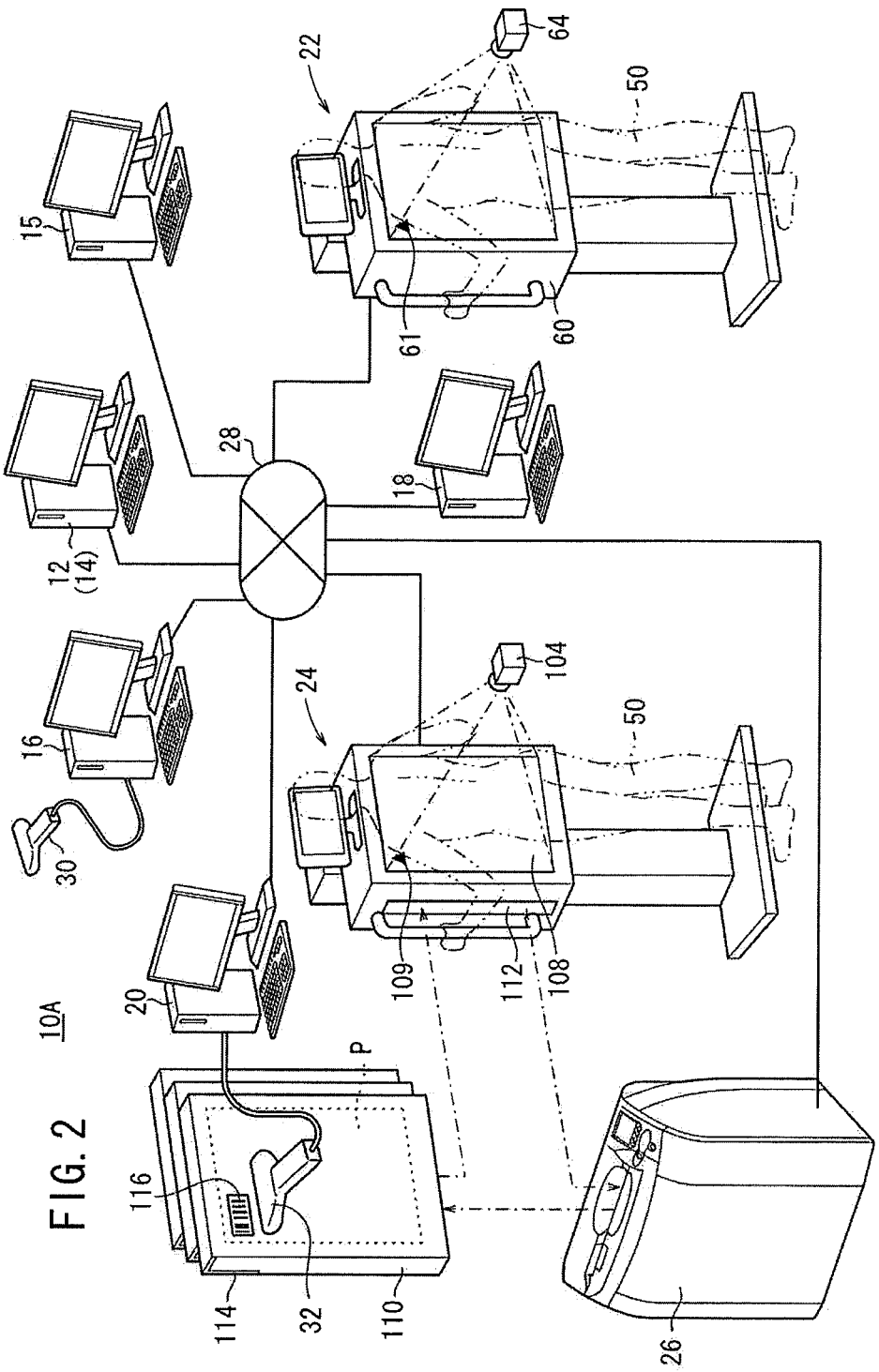
FIG. 2 is a schematic perspective view of the first system.

FIGS. 1 and 2 show a configuration of a radiation image capturing system 10A according to a first embodiment of the present invention (hereinafter referred to as "first system 10A"). As shown in FIGS. 1 and 2, the first system 10A comprises a hospital information system (HIS) 12 for managing medical information in a hospital, a radiology information system (RIS) 14 for managing radiation image capturing processes performed in the radiological department of the hospital under the management of the HIS 12, a viewer 15 for displaying radiation images to be interpreted by the doctor for diagnosis, a host console (image correcting apparatus) 16 placed in a control room near image capturing rooms in the radiological department, for managing various image capturing apparatus of different specifications, a first console 18 and a second console 20 placed in the control room for controlling particular image capturing apparatus, respectively, a first image capturing apparatus 22 for being controlled by the first console 18, a second image capturing apparatus 24 for being controlled by the second console 20, and a reading apparatus 26 for being controlled by the second console 20 for reading radiation image information captured by the second image capturing apparatus 24. The above components of the first system 10A are interconnected by an in-house network 28 in the hospital. If necessary, other consoles, other image capturing apparatus, and components may also be connected to the in-house network 28.

The host console 16 acquires patient information such as the name, gender, age, etc. of a patient which has been set using the HIS 12, and image capturing instruction information such as a method of capturing a radiation image, a body region to be imaged, and an image capturing apparatus to be used to capture a radiation image, which has been set by the doctor or radiological technician using the RIS 14 through the in-house network 28, and supplies the acquired information to the first console 18 or the second console 20. The host console 16 may be programmed to perform the processing sequence of the first console 18 or the second console 20. If the host console 16 is programmed to perform the processing sequence of the first console 18 or the second console 20, then since the first console 18 or the second console 20 may be dispensed with, the radiation image capturing system will become less costly. To the host console 16 and the second console 20, there are connected respective bar-code readers 30, 32 for acquiring ID information for identifying a radiation detector, described later, to be used in the first image capturing apparatus 22.

Figure 3:
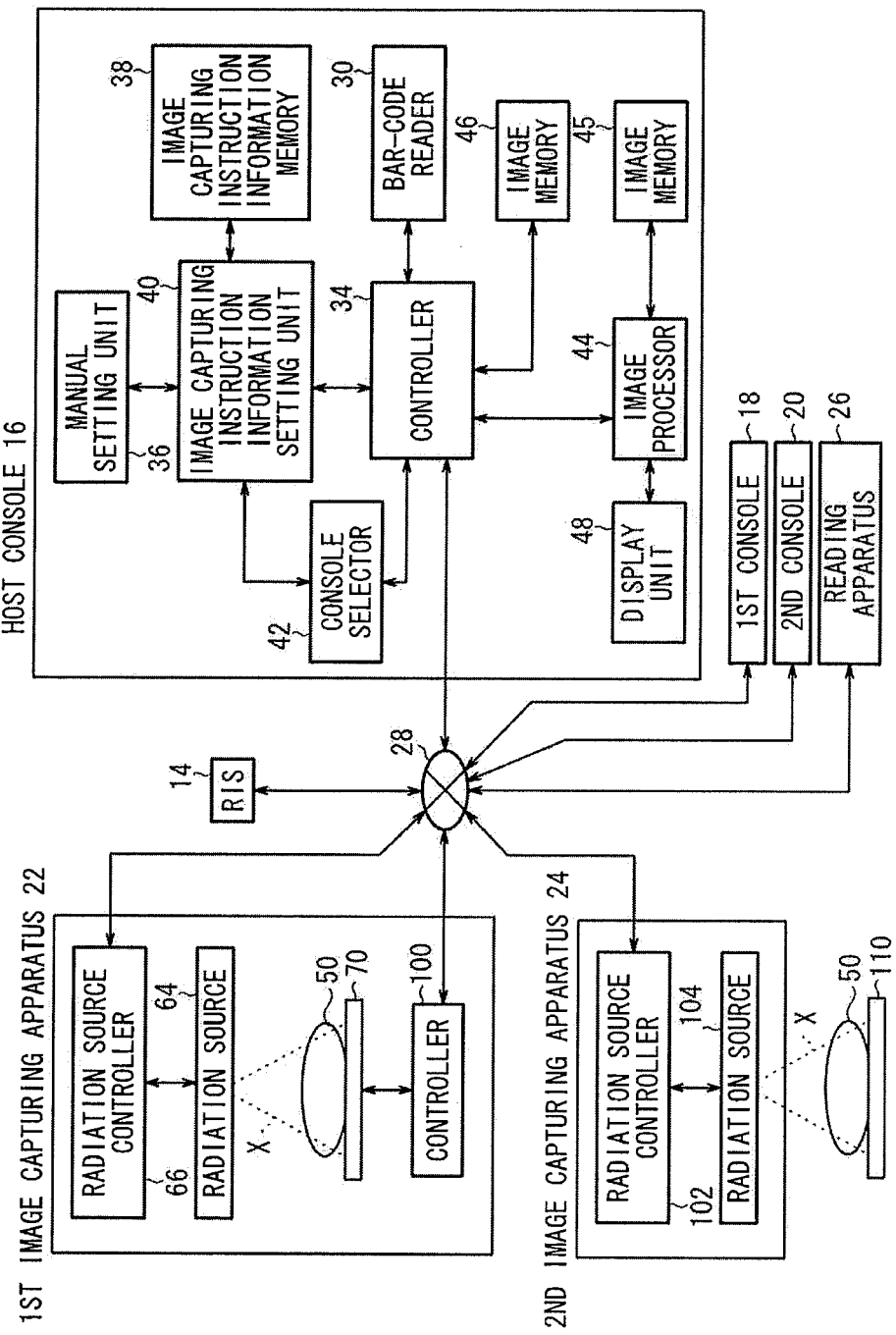
FIG. 3 is a block diagram of an assembly of a host console, a first image capturing apparatus, and a second image capturing apparatus of the first system.

FIG. 3 shows in block form an assembly of the host console 16, the first image capturing apparatus 22, and the second image capturing apparatus 24.

The host console 16 has a controller 34 which sends information to and receives information from the RIS 14, the first console 18, the second console 20, the first image capturing apparatus 22, the second image capturing apparatus 24, and the reading apparatus 26 through the in-house network 28. The host console 16 comprises a manual setting unit 36, an image capturing instruction information setting unit 40 for setting image capturing instruction information through the manual setting unit 36 or receiving image capturing instruction information set by the RIS 14 and storing the image capturing instruction information in an image capturing instruction information memory 38, a console selector 42 for selecting the first console 18 or the second console 20 for processing radiation image information according to the set image capturing instruction information and supplying the corresponding image capturing instruction information to the first console 18 or the second console 20 which is selected, an image processor (image correcting device) 44 for performing an image processing process including magnification correction on radiation image information acquired from the first image capturing apparatus 22 and the second image capturing apparatus 24, an image memory 45 for storing the processed radiation image information, an image memory 46 for storing uncorrected radiation image information acquired from the first image capturing apparatus 22 and the second image capturing apparatus 24, and a display unit 48 for displaying the processed radiation image information.

The first console 18 and the second console 20 have essentially the same functions as the host console 16 except for the controller 34 for acquiring image capturing instruction information from the RIS 14 and the console selector 42. The configurations of the host console 16, the first console 18, and the second console 20 may not necessarily be different from each other, but may be identical to each other.

The first image capturing apparatus 22 is an upstanding image capturing apparatus for capturing a radiation image of the chest or the like of a subject 50. The first image capturing apparatus 22 comprises a radiation source 64 for being controlled by a radiation source controller 66 and an image capturing base 60 disposed in confronting relation to the radiation source 64. The image capturing base 60 houses therein a radiation detector 70 which comprises a solid-state detecting device to be described later. The image capturing base 60 has a marker 61 disposed on an image capturing surface thereof against which the subject 50 to be imaged by the first image capturing apparatus 22 are held. When a radiation image of the subject 50 is captured by the first image capturing apparatus 22, a radiation image of the marker 61 is also captured thereby. The radiation source controller 66 controls the radiation source 64 according to image capturing conditions set by the host console 16.

Figure 4:
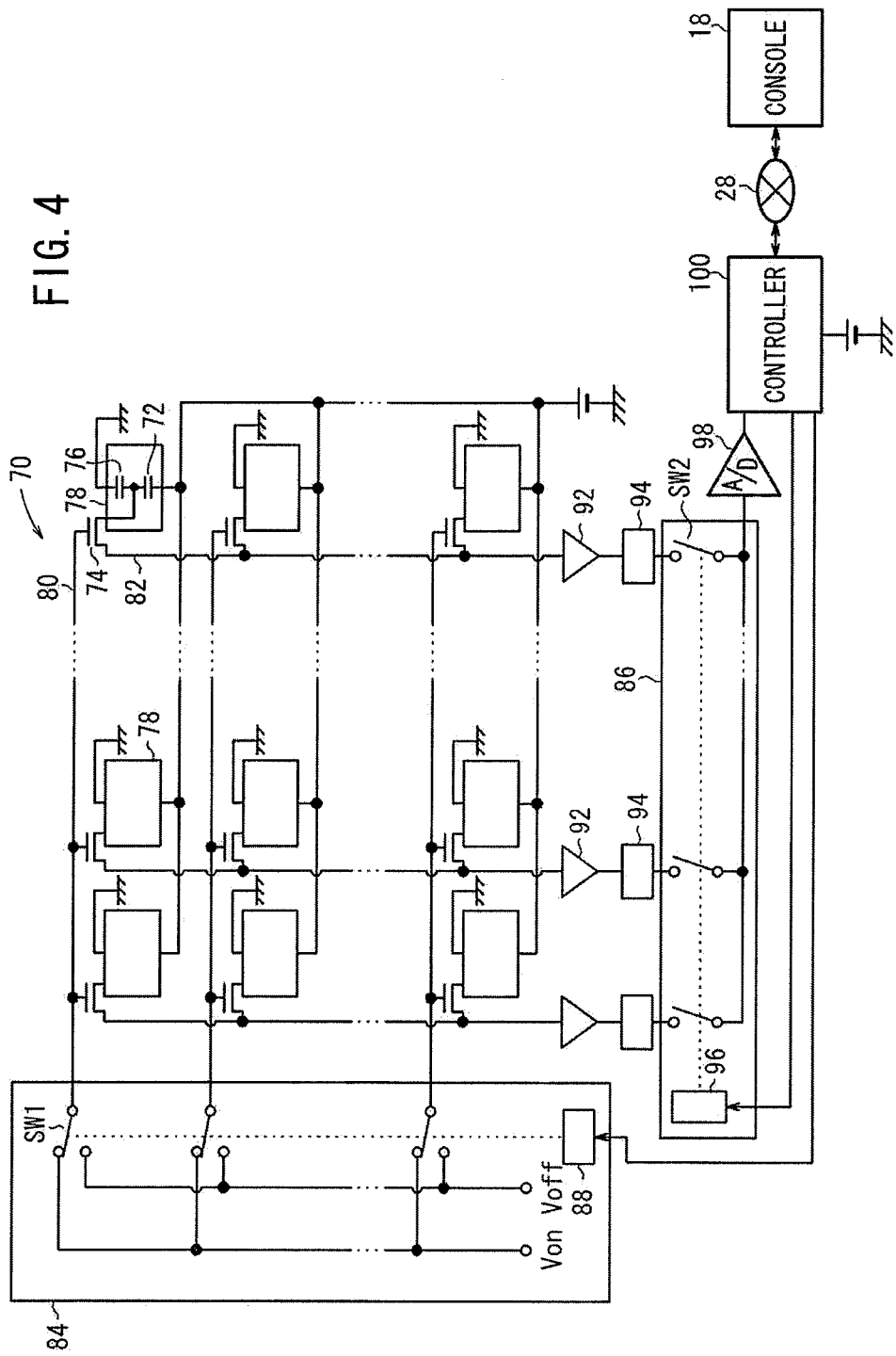
FIG. 4 is a block diagram of a circuit arrangement of a radiation detector used in the first system.

FIG. 4 shows in block form a circuit arrangement of the radiation detector 70 housed in the image capturing base 60.

The radiation detector 70 comprises an array of thin-film transistors (TFTs) 74 arranged in rows and columns, a photoelectric conversion layer 72 made of a material such as amorphous selenium (a-Se) for generating electric charges upon detection of a radiation, the photoelectric conversion layer 72 being disposed over the array of TFTs 74, and an array of storage capacitors 76 connected to the photoelectric conversion layer 72. When the radiation is applied to the radiation detector 70, the photoelectric conversion layer 72 generates electric charges, and the storage capacitors 76 store the generated electric charges. Then, the TFTs 74 are turned on along each row at a time to read the electric charges from the storage capacitors 76 as an image signal. In FIG. 4, the photoelectric conversion layer 72 and one of the storage capacitors 76 are shown as a pixel 78, and the pixel 78 is connected to one of the TFTs 74. Details of the other pixels 78 are omitted from illustration. Since amorphous selenium tends to change its structure and lose its function at high temperatures, it needs to be used within a certain temperature range. Therefore, some means for cooling the radiation detector 70 should preferably be provided in the image capturing base 60.

The TFTs 74 connected to the respective pixels 78 are connected to respective gate lines 80 extending parallel to the rows and respective signal lines 82 extending parallel to the columns. The gate lines 80 are connected to a line scanning driver 84, and the signal lines 82 are connected to a multiplexer 86 serving as a reading circuit.

The gate lines 80 are supplied with control signals Von, Voff for turning on and off the TFTs 74 along the rows from the line scanning driver 84. The line scanning driver 84 comprises a plurality of switches SW1 for switching between the gate lines 80 and an address decoder 88 for outputting a selection signal for selecting one of the switches SW1 at a time. The address decoder 88 is supplied with an address signal from a controller 100.

The signal lines 82 are supplied with electric charges stored in the storage capacitors 76 of the pixels 78 through the TFTs 74 arranged in the columns. The electric charges supplied to the signal lines 82 are amplified by amplifiers 92 connected respectively to the signal lines 82. The amplifiers 92 are connected through respective sample and hold circuits 94 to the multiplexer 86. The multiplexer 86 comprises a plurality of switches SW2 for successively switching between the signal lines 82 and an address decoder 96 for outputting a selection signal for selecting one of the switches SW2 at a time. The address decoder 96 is supplied with an address signal from the controller 100. The multiplexer 86 has an output terminal connected to an A/D converter 98. A radiation image signal generated by the multiplexer 86 based on the electric charges from the sample and hold circuits 94 is converted by the A/D converter 98 into a digital image signal representing radiation image information, which is supplied to the controller 100. The controller 100 supplies the acquired radiation image information through the in-house network 28 to the first console 18 which controls the first image capturing apparatus 22.

The second image capturing apparatus 24 is an upstanding image capturing apparatus for capturing a radiation image of the chest or the like of a subject 50. The second image capturing apparatus 24 comprises a radiation source 104 for being controlled by a radiation source controller 102 and an image capturing base 108 disposed in confronting relation to the radiation source 104. The image capturing base 108 has a marker 109 disposed on an image capturing surface thereof against which the subject 50 to be imaged by the second image capturing apparatus 24 is held. When a radiation image of the subject 50 is captured by the second image capturing apparatus 24, a radiation image of the marker 109 is also captured thereby. The marker 109 on the image capturing base 108 is identical in dimensions and shape to the marker 61 on the image capturing base 60 of the first image capturing apparatus 22. The image capturing base 108 has a slot 112, defined in a side wall thereof, through which a cassette 110 housing a stimulable phosphor panel P therein can be loaded into the image capturing base 108. The second image capturing apparatus 24 is controlled by the second console 20 through the in-house network 28. The second image capturing apparatus 24 has different specifications from the first image capturing apparatus 22. The radiation source controller 102 controls the radiation source 104 according to image capturing conditions set by the host console 16.

The stimulable phosphor panel P comprises a support body and a stimulable phosphor layer disposed on the support body. The stimulable phosphor layer stores the energy of a radiation X that is applied thereto. When the stimulable phosphor layer is irradiated with stimulating light, it emits stimulated light depending on the stored energy. When the stimulable phosphor layer is irradiated with a certain amount of erasing light, it discharges any remaining energy stored therein and can be reused.

The stimulable phosphor panel P housed in the cassette 110 is removable from the cassette 110 when a lid 114 on the cassette 110 is opened. A bar code 116 which records therein identification information including an identification number for identifying the stimulable phosphor panel P housed in the cassette 110, the size of the stimulable phosphor panel P, the sensitivity of the stimulable phosphor panel P, etc. is applied to an outer surface of the cassette 110. The bar code 116 can be read by the bar-code reader 32 connected to the second console 20 or the bar-code reader 30 connected to the host console 16.

Figure 5:
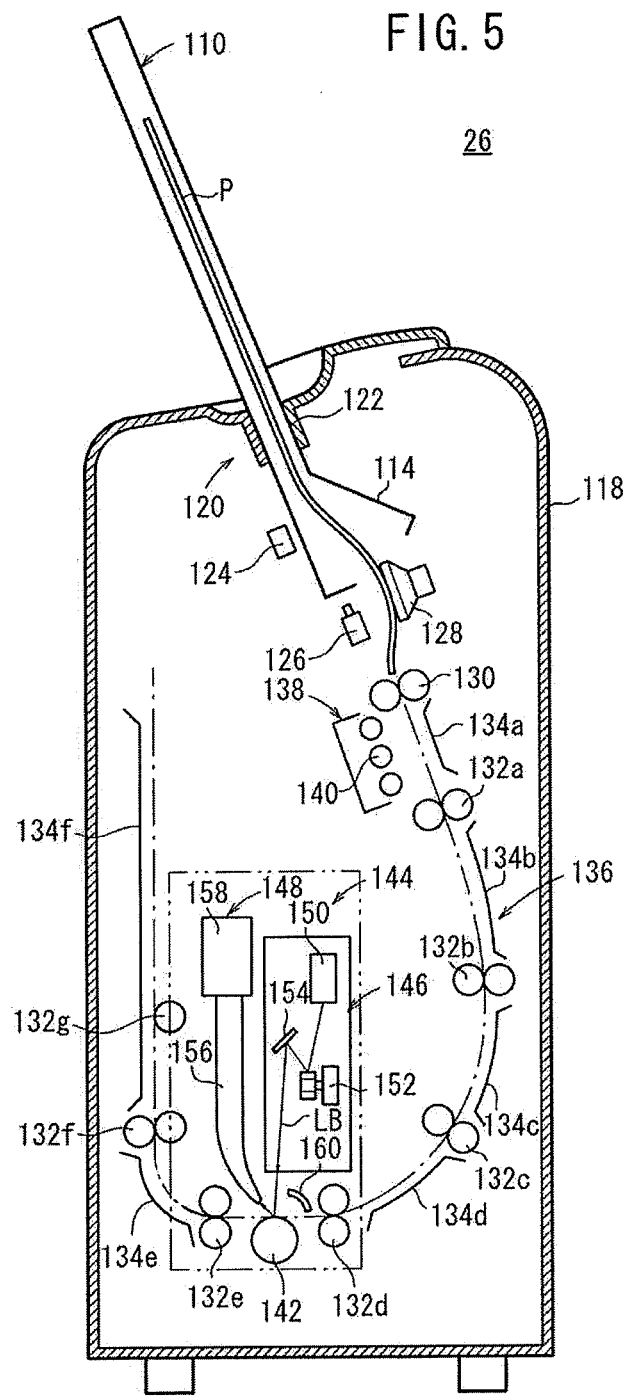
FIG. 5 is a vertical cross-sectional view of a reading apparatus of the first system.

Radiation image information that is recorded in the stimulable phosphor panel P is read by the reading apparatus 26 which is constructed as shown in FIG. 5. The reading apparatus 26, together with the second image capturing apparatus 24, is controlled by the second console 20 through the in-house network 28.

As shown in FIG. 5, the reading apparatus 26 has a cassette loader 120 disposed in an upper portion of a casing 118 and having a loading slot 122 for receiving therein the cassette 110 which houses therein the stimulable phosphor panel P with recorded radiation image information. The casing 118 of the reading apparatus 26 accommodates therein, near the loading slot 122, a bar-code reader 124 for reading the identification information recorded in the bar code 116 on the cassette 110, an unlock mechanism 126 for unlocking the lid 114 of the cassette 110, a suction cup 128 for attracting and removing the stimulable phosphor panel P from the cassette 110 at the time the lid 114 is opened, and a pair of nip rollers 130 for gripping and feeding the stimulable phosphor panel P removed by the suction cup 128.

The nip rollers 130 are followed by a plurality of feed rollers 132a through 132g and a plurality of guide plates 134a through 134f which jointly make up a curved feed path 136. The curved feed path 136 extends downwardly from the cassette loader 120, then extends substantially horizontally at its lowermost portion, and then extends substantially vertically upwardly. The curved feed path 136 thus shaped is effective to make the reading apparatus 26 small in size.

Between the nip rollers 130 and the feed rollers 132a, there is disposed an erasing unit 138 for erasing radiation image information remaining in the stimulable phosphor panel P from which desired radiation image information has been read. The erasing unit 138 has a plurality of erasing light sources 140 such as cold cathode-ray tubes or the like for emitting erasing light.

A platen roller 142 is disposed between the feed rollers 132d, 132e which are positioned in the lowermost portion of the curved feed path 136. The platen roller 142 is disposed beneath a scanning unit 144 for reading the desired radiation image information recorded in the stimulable phosphor panel P.

The scanning unit 144 comprises a stimulator 146 for emitting a laser beam LB as stimulating light to scan the stimulable phosphor panel P and a reader 148 for reading stimulated light having radiation image information emitted from the stimulable phosphor panel P which is stimulated by the laser beam LB.

The stimulator 146 comprises a laser oscillator 150 for outputting the laser beam LB, a rotary polygon mirror 152 for deflecting the laser beam LB in a main scanning direction across the stimulable phosphor panel P, and a reflecting mirror 154 for reflecting the laser beam LB to the stimulable phosphor panel P as it passes over the platen roller 142.

The reader 148 comprises a light guide 156 having a lower end disposed near the stimulable phosphor panel P over the platen roller 142, and a photomultiplier 158 connected to an upper end of the light guide 156 for converting the stimulated light from the stimulable phosphor panel P into an electric signal which represents the radiation image information stored in the stimulable phosphor panel P. A light collecting mirror 160 for collecting the stimulated light more efficiently from the stimulable phosphor panel P is disposed near the lower end of the light guide 156. The photomultiplier 158 supplies the electric signal representing the radiation image information to the second console 20 through the in-house network 28.

A recumbent image capturing apparatus which may employ the radiation detector 70 or the stimulable phosphor panel P may be connected to the in-house network 28. Furthermore, image capturing apparatus of other specifications, such as a CT apparatus, an MR apparatus, etc. may also be connected to the in-house network 28, and consoles for controlling these image capturing apparatus may also be connected to the in-house network 28.

The first system 10A is basically constructed as described above. Operation of the first system 10A will be described below with reference to FIGS. 6 through 11.

First, patient information such as the name, gender, age, etc. of a patient is set using the HIS 12 (step S1 shown in FIG. 6), and image capturing instruction information such as a method of capturing a radiation image, a body region to be imaged, and an image capturing apparatus to be used to capture a radiation image, is set in relation to the patient information using the RIS 14 (step S2).

The controller 34 of the host console 16 that is installed in the radiological department acquires the patient information and the image capturing instruction information from the RIS 14 via the in-house network 28 (step S3). The radiological technician sets and changes the image capturing instruction information using the manual setting unit 36 of the host console 16. For example, the radiological technician changes from an image capturing apparatus set by the doctor using the RIS 14 to an image capturing apparatus suitable for a body region to be imaged and the condition of the patient. The image capturing instruction information setting unit 40 stores the patient information and the image capturing instruction information which have been acquired or the image capturing instruction information which has been changed or newly set into the image capturing instruction information memory 38.

Then, the image capturing instruction information setting unit 40 of the host console 16 reads the patient information and the image capturing instruction information from the image capturing instruction information memory 38 (step S4). The console selector 42 selects the first console 18 for controlling the first image capturing apparatus 22, the second console 20 for controlling the second image capturing apparatus 24, or another console connected to the in-house network 28 according to the read image capturing instruction information (step S5).

At this time, the console selector 42 determines whether the processor for controlling the image capturing apparatus that is indicated by the image capturing instruction information is capable of performing its processing sequence or not. For example, if the processor is controlling the image capturing apparatus to perform an image capturing process or processing radiation image information acquired from the image capturing apparatus, and hence is unable to immediately perform a next cycle of processing sequence, then the console selector 42 judges that the processor is incapable of performing its processing sequence. Furthermore, if the processor is suffering a failure or the image capturing apparatus controlled by the processor is suffering a failure, then the console selector 42 also judges that the processor is incapable of performing its processing sequence. When the processor is judged as being incapable of performing its processing sequence, the console selector 42 searches for another processor which is capable of capturing radiation image information according to the image capturing instruction information and also of performing its processing sequence.

After the processor capable of performing its processing sequence is selected, the controller 34 of the host console 16 sends the patient information and the image capturing instruction information to the first console 18, the second console 20, or another console which has been selected (step S6), confirms the completion of the sending of the patient information and the image capturing instruction information, and deletes the patient information and the image capturing instruction information from the image capturing instruction information memory 38.

If the host console 16 serves as a processor capable of performing processing sequences for a plurality of image capturing apparatus of different specifications, then the host console 16 may be selected as a console, instead of the first console 18 or the second console 20, for performing a processing sequence for the first image capturing apparatus 22 or the second image capturing apparatus 24.

The console to which the patient information and the image capturing instruction information have been sent now performs a process of capturing radiation image using the image capturing apparatus under its control, according to the image capturing instruction information (step S7).

First, a process of capturing radiation image of the subject 50 with the first image capturing apparatus 22 controlled by the first console 18 will be described below with reference to FIG. 7.

Figure 7:
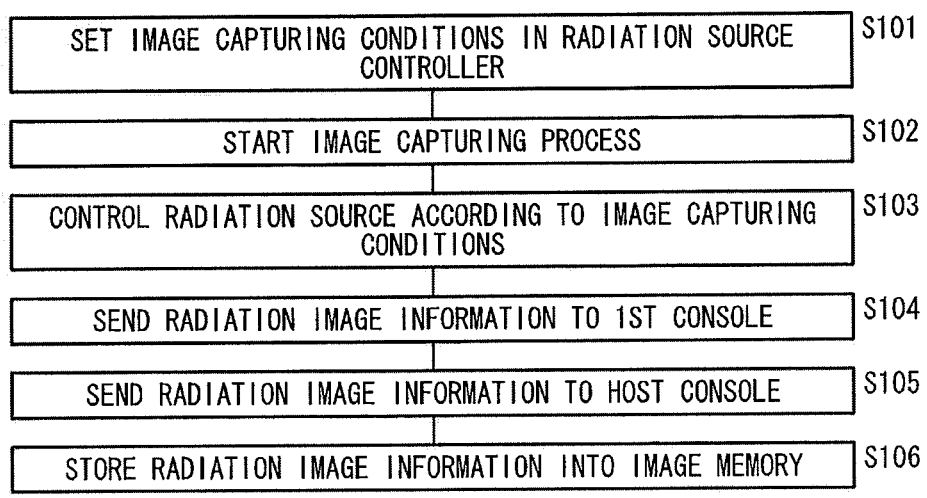
FIG. 7 is a flowchart of an operating sequence of the first image capturing apparatus.

When the first console 18 receives the image capturing instruction information from the host console 16, the first console 18 sets image capturing conditions including a tube voltage, a tube current, and an irradiation time included in the image capturing instruction information in the radiation source controller 66 of the first image capturing apparatus 22 (step S101 in FIG. 7).

After having positioned the subject 50 in a given position on the image capturing base 60, the radiological technician operates an image capturing switch, not shown, to start an image capturing process (step S102). The radiation source controller 66 controls the radiation source 64 according to the set image capturing conditions to apply the radiation X to the subject 50 (step S103). The radiation X passes through the subject 50 and is applied to the radiation detector 70. The image capturing base 60 has the marker 61 on the image capturing surface for the subject 50. The radiation X also passes through the marker 61 and is applied to the radiation detector 70.

The radiation X is converted into electric signals by the photoelectric conversion layer 72 of the pixels 78 of the radiation detector 70 (FIG. 4). The electric signals are stored as electric charges in the storage capacitors 76. The stored electric charges, which represent radiation image information of the patient 50 and the marker 61, are read from the storage capacitors 76 according to address signals which are supplied from the controller 100 to the line scanning driver 84 and the multiplexer 86.

Specifically, in response to the address signal supplied from the controller 100, the address decoder 88 of the line scanning driver 84 outputs a selection signal to select one of the switches SW1, which supplies the control signal Von to the gates of the TFTs 74 connected to the gate line 80 corresponding to the selected switch SW1. In response to the address signal supplied from the controller 100, the address decoder 96 of the multiplexer 86 outputs a selection signal to successively turn on the switches SW2 to switch between the signal lines 82 for thereby reading the electric charges as radiation image information stored in the storage capacitors 76 of the pixels 78 connected to the selected gate line 80, through the signal lines 82.

The electric charges as radiation image information read from the storage capacitors 76 of the pixels 78 connected to the selected gate line 80 are amplified by the respective amplifiers 92, sampled by the sample and hold circuits 94, and supplied to the multiplexer 86. Based on the supplied electric charges, the multiplexer 86 generates and supplies a radiation image signal to the A/D converter 98, which converts the radiation image signal into a digital signal. The digital signal which represents the radiation image information is transmitted from the controller 100 to the first console 18 through the in-house network 28 (step S104).

Similarly, the address decoder 88 of the line scanning driver 84 successively turns on the switches SW1 to switch between the gate lines 80 according to the address signal supplied from the controller 100. The electric charges as radiation image information stored in the storage capacitors 76 of the pixels 78 connected to the successively selected gate lines 80 are read through the signal lines 82, and processed by the multiplexer 86 and the A/D converter 98 into digital signals, which are transmitted from the controller 100 to the first console 18 through the in-house network 28 (step S104).

The first console 18 processes the radiation image information represented by the received digital signals depending on the specifications of the first image capturing apparatus 22. Then, if necessary, the first console 18 displays a radiation image based on the processed radiation image information for the radiological technician to confirm the radiation image, and then transmits the processed radiation image information D1 of the subject 50 and the marker 61 to the host console 16 through the in-house network 28 (step S105). The controller 34 of the host console 16 temporarily stores the radiation image information D1 into the image memory 46 (step S106).

A process of capturing a chest image of the subject 50 with the second image capturing apparatus 24 controlled by the second console 20 will be described below with reference to a flowchart of FIG. 8.

Figure 8:
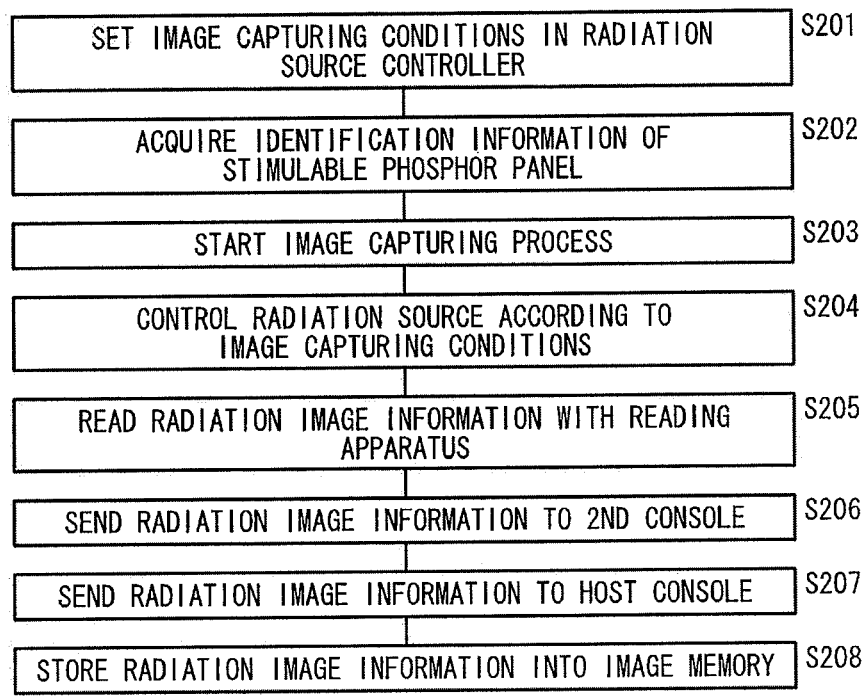
FIG. 8 is a flowchart of an operating sequence of the second image capturing apparatus.

When the second console 20 receives the image capturing instruction information from the host console 16, the second console 20 sets image capturing conditions including a tube voltage, a tube current, and an irradiation time included in the image capturing instruction information, in the radiation source controller 102 of the second image capturing apparatus 24 (step S201 in FIG. 8).

The radiological technician uses the bar-code reader 32 connected to the second console 20 to read the bar code 116 attached to the cassette 110, thereby acquiring identification information including an identification number for identifying the stimulable phosphor panel P housed in the cassette 110, the size of the stimulable phosphor panel P, the sensitivity of the stimulable phosphor panel P, etc. (step S202).

After having loaded the cassette 110 into the slot 112 of the second image capturing apparatus 24, the radiological technician operates an image capturing switch, not shown, to start an image capturing process (step S203). The radiation source controller 102 controls the radiation source 104 according to the set image capturing conditions to apply the radiation X to the subject 50 (step S204). The radiation X that has passed through the subject 50 is applied to the stimulable phosphor panel P housed in the cassette 110. As a result, radiation image information of the subject 50 is recorded in the stimulable phosphor panel P.

The image capturing base 108 has the marker 109 on the image capturing surface for the subject 50. The radiation X also passes through the marker 109 and is applied to the stimulable phosphor panel P, recording radiation image information of the marker 109 in the stimulable phosphor panel P.

The radiological technician then removes the cassette 110 housing therein the stimulable phosphor panel P with the recorded radiation image information from the second image capturing apparatus 24, and thereafter loads the cassette 110 into the cassette loader 120 of the reading apparatus 26.

When the cassette 110 is loaded into the cassette loader 120, the bar-code reader 124 in the cassette loader 120 reads the bar code 116 applied to the cassette 110 to acquire the identification information including the identification number, the size, the sensitivity, etc. of the stimulable phosphor panel P. The acquired identification information is compared with the identification information read by the bar-code reader 32 connected to the second console 20 to confirm the correspondence between the subject 50 and the radiation image information.

After the identification information is read, the unlock mechanism 126 is actuated to unlock and open the lid 114. The suction cup 128 attracts the stimulable phosphor panel P, removes the stimulable phosphor panel P out of the cassette 110, and feeds the stimulable phosphor panel P between the nip rollers 130. The stimulable phosphor panel P which is gripped by the nip rollers 130 is then fed through the curved feed path 136 made up of the feed rollers 132a through 132g and the guide plates 134a through 134f to a position beneath the scanning unit 144.

Beneath the scanning unit 144, the stimulable phosphor panel P is fed substantially horizontally in an auxiliary scanning direction by the feed rollers 132d, 132e. At the same time, the laser beam LB output from the laser oscillator 150 of the stimulator 146 is reflected and deflected by the polygon mirror 152 that is rotating at a high speed, and then guided by the reflecting mirror 154 to the stimulable phosphor panel P whose lower surface is supported by the platen roller 142, thereby scanning the stimulable phosphor panel P in a main scanning direction that is perpendicular to the auxiliary scanning direction.

By being irradiated with the laser beam LB, the stimulable phosphor panel P is stimulated to emit stimulated light representative of the radiation image information recorded therein. The stimulated light is applied directly or via the light collecting mirror 160 to the lower end of the light guide 156 which is disposed near the stimulable phosphor panel P and extends in the main scanning direction. The stimulated light which has entered the light guide 156 is repeatedly reflected in the light guide 156 and guided to the photomultiplier 158 on the upper end. The photomultiplier 158 converts the stimulated light into an electric signal representative of the radiation image information recorded in the stimulable phosphor panel P. In this manner, the radiation image information of the subject 50 and the marker 109 recorded in the stimulable phosphor panel P is read by the scanning unit 144 of the reading apparatus 26 (step S205).

The radiation image information thus read by the scanning unit 144 is transmitted to the second console 20 through the in-house network 28 (step S206). The second console 20 processes the received radiation image information depending on the specifications of the second image capturing apparatus 24. Then, if necessary, the second console 20 displays a radiation image based on the processed radiation image information for the radiological technician to confirm the radiation image, and then transmits the processed radiation image information D2 of the subject 50 and the marker 109 to the host console 16 through the in-house network 28 (step S207). The controller 34 of the host console 16 temporarily stores the radiation image information D2 into the image memory 46 (step S208).

Then, the controller 34 reads the radiation image information D1 acquired using the first image capturing apparatus 22 and the radiation image information D2 acquired using the second image capturing apparatus 24 from the image memory 46, and controls the image processor 44 to perform a desired image processing process on the radiation image information D1 and the radiation image information D2. A process of capturing radiation images of the same subject 50 at different times with the first image capturing apparatus 22 and the second image capturing apparatus 24, respectively, correcting the magnifications of the captured radiation images so as to be equal to each other, and displaying the radiation images at the same magnification on the display unit 48 for the doctor to make a comparative diagnosis, will be described below with reference to FIGS. 9 through 11.

Figure 9:
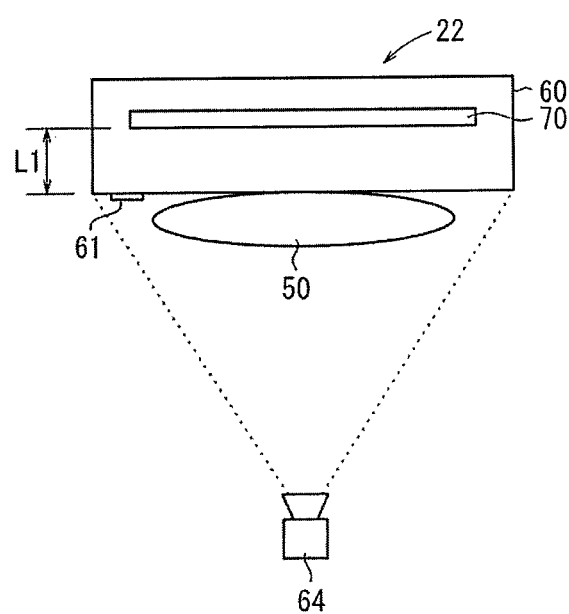
FIG. 9 is a schematic diagram showing the positional relationship between a subject, a marker, and the radiation detector in the first image capturing apparatus.
Figure 10:
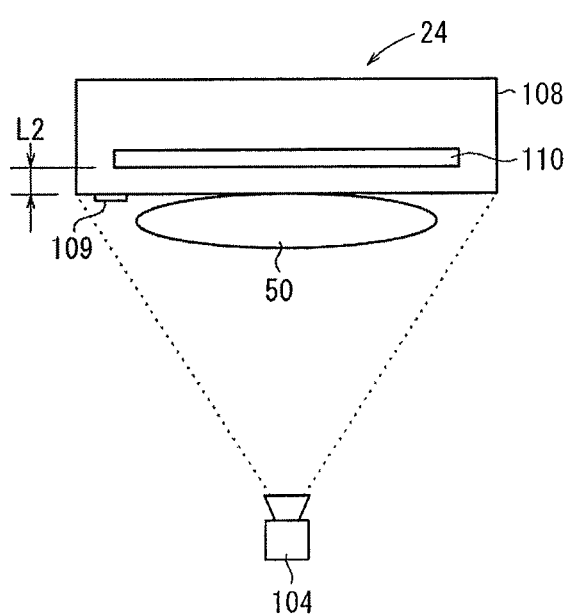
FIG. 10 is a schematic diagram showing the positional relationship between a subject, a marker, and a stimulable phosphor panel in the second image capturing apparatus.
Figure 11:
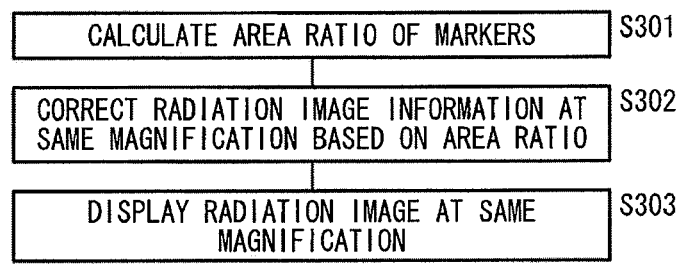
FIG. 11 is a flowchart of a magnification correction process performed by a controller of the host console.

FIG. 9 schematically shows the positional relationship between the subject 50, the marker 61, and the radiation detector 70 in the first image capturing apparatus 22, and FIG. 10 schematically shows the positional relationship between the subject 50, the marker 109, and the stimulable phosphor panel P in the second image capturing apparatus 24.

As shown in FIG. 9, the image capturing surface of the image capturing base 60, against which the subject 50 to be imaged by the first image capturing apparatus 22 are held, is spaced from the radiation detector 70 housed in the image capturing base 60 by a distance L1. As shown in FIG. 10, the image capturing surface of the image capturing base 108, against which the subject 50 to be imaged by the second image capturing apparatus 24 are held, is spaced from the stimulable phosphor panel P placed in the cassette 110 housed in the image capturing base 108 by a distance L2. Since the first image capturing apparatus 22 and the second image capturing apparatus 24 are structurally different from each other, the distances L1, L2 are usually different from each other. Therefore, radiation images of the same subject 50 captured by the first image capturing apparatus 22 and the second image capturing apparatus 24 are usually of different sizes.

The image processor 44 reads the radiation image information of the marker 61 on the image capturing surface of the image capturing base 60 of the first image capturing apparatus 22 and the radiation image information of the marker 109 on the image capturing surface of the image capturing base 108 the second image capturing apparatus 24 from the image memory 46, and calculates respective areas S1, S2 of the respective markers 61, 109 from the read radiation image information of the markers 61, 109. Then, the image processor 44 calculates an area ratio S1/S2 of the calculated areas S1, S2 (step S301 shown in FIG. 11).

Thereafter, if the radiation image information D2 acquired from the second image capturing apparatus 24 is to be of the same magnification as the radiation image information D1 acquired from the first image capturing apparatus 22, for example, then the image processor 44 performs a corrective process for multiplying the radiation image information D2 by the area ratio S1/S2 (step S302). As a result, the image processor 44 produces radiation image information D2' which is of the same magnification as the radiation image information D1.

The image processor 44 then outputs the magnification-adjusted radiation image information D2, to the display unit 48, which displays a corresponding radiation image (step S303). The radiological technician can now confirm the displayed radiation image of the subject 50. The host console 16 sends the magnification-adjusted radiation image information D2' and the radiation image information D1 whose magnification has not been adjusted through the in-house network 28 to the viewer 15, which displays respective radiation images based on the radiation image information D2' and the radiation image information D1. The doctor then interprets for diagnosis the radiation images of the predetermined region that are displayed by the viewer 15.

A plurality of spaced markers 61 may be disposed on the image capturing base 60 of the first image capturing apparatus 22, and a plurality of spaced markers 109 may be disposed on the image capturing base 108 of the second image capturing apparatus 24. The distances between the spaced markers 61, 109 in the radiation images may be calculated, and the radiation image information D1 and the radiation image information D2 may be corrected based on the ratio of those distances.

In the present embodiment, the host control 16 corrects the radiation image information such that the radiation image information D1 and the radiation image information D2 will be of the same magnification. However, one or both of the first console 18 and the second console 20 may have the image processor 44 and the image memory 46 for correcting the radiation image information such that the radiation image information D1 and the radiation image information D2 will be of the same magnification.

A radiation image capturing system 10B according to a second embodiment of the present invention (hereinafter referred to as "second system 10B") will be described below with reference to FIGS. 12 through 17.

Figure 12:
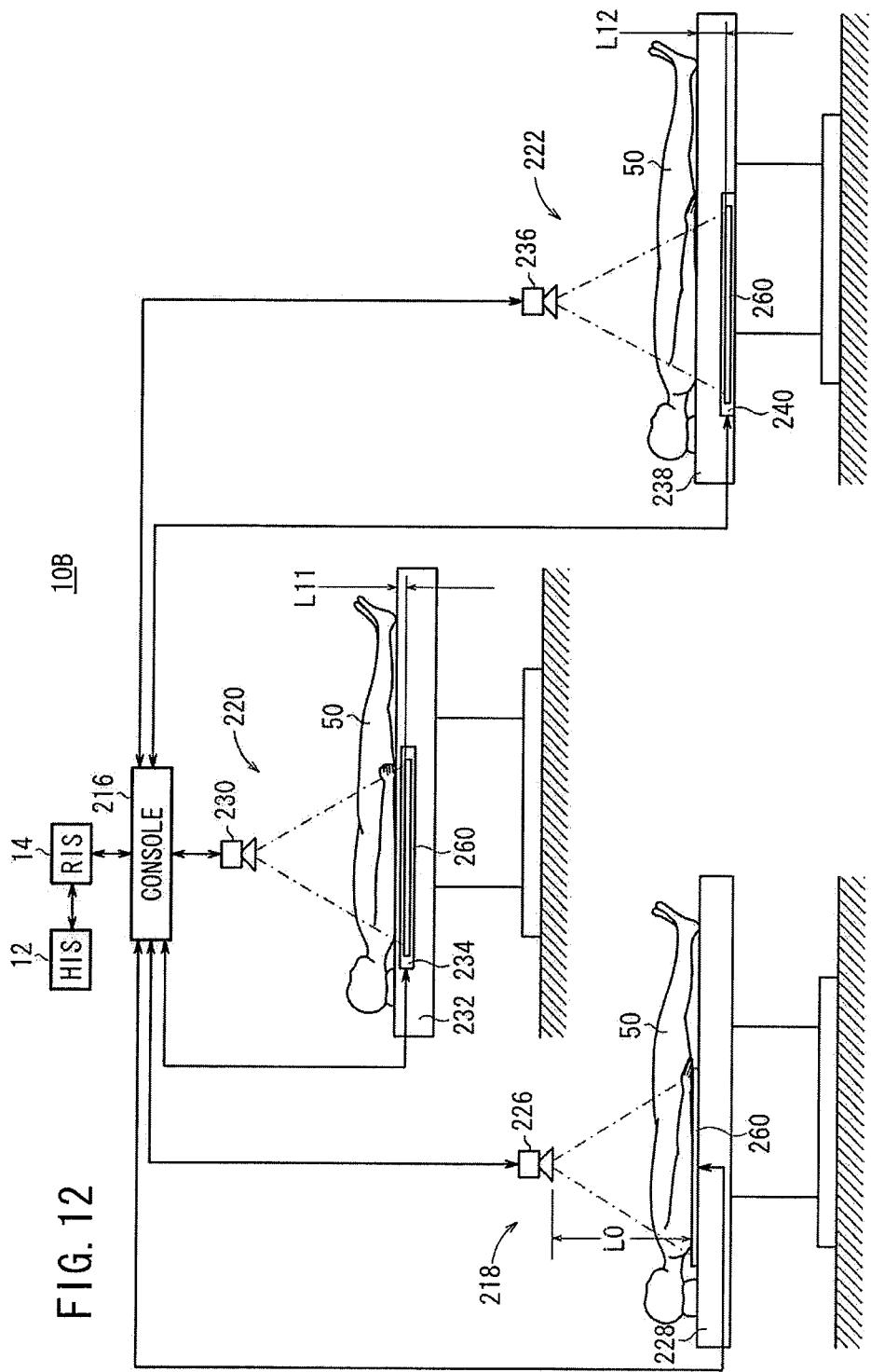
FIG. 12 is a schematic view of a second system according to the present invention.

As shown in FIG. 12, the second system 10B comprises, in addition to the HIS 12 and the RIS 14 referred to above, a console (processor) 216 placed in a control room near image capturing rooms in the radiological department, for managing various image capturing apparatus of different specifications, an eleventh image capturing apparatus 218, a twelfth image capturing apparatus 220, and a thirteenth image capturing apparatus 222 which are interconnected by the in-house network 28 in the hospital, as described later. If necessary, other consoles, other image capturing apparatus, and components may also be connected to the in-house network 28.

The console 216 acquires patient information such as the name, gender, age, etc. of a patient which has been set using the HIS 12, and image capturing instruction information such as a method of capturing a radiation image, a body region to be imaged, and an image capturing apparatus to be used to capture a radiation image, which has been set by the doctor or radiological technician using the RIS 14 through the in-house network 28.

The eleventh image capturing apparatus 218 comprises a radiation source 226 and an image capturing base 228 on which an electronic cassette (radiation conversion device, radiation detecting apparatus) 260 is placed. The twelfth image capturing apparatus 220 comprises a radiation source 230 and an image capturing base 232 having a slot 234 defined therein which is spaced from an upper surface of the image capturing base 232 by a distance L11. An electronic cassette 260 can be loaded through the slot 234 into the image capturing base 232. The thirteenth image capturing apparatus 222 comprises a radiation source 236 and an image capturing base 238 having a slot 240 defined therein which is spaced from an upper surface of the image capturing base 238 by a distance L12. An electronic cassette 260 can be loaded through the slot 240 into the image capturing base 238. In FIG. 12, the slot 234 is positioned such that when the electronic cassette 260 is loaded through the slot 234 into the image capturing base 232, an image capturing surface of the electronic cassette 260 is spaced from the upper surface of the image capturing base 232 by the distance L11. Similarly, the slot 240 is positioned such that when the electronic cassette 260 is loaded through the slot 240 into the image capturing base 238, an image capturing surface of the electronic cassette 260 is spaced from the upper surface of the image capturing base 238 by the distance L12.

Figure 13:
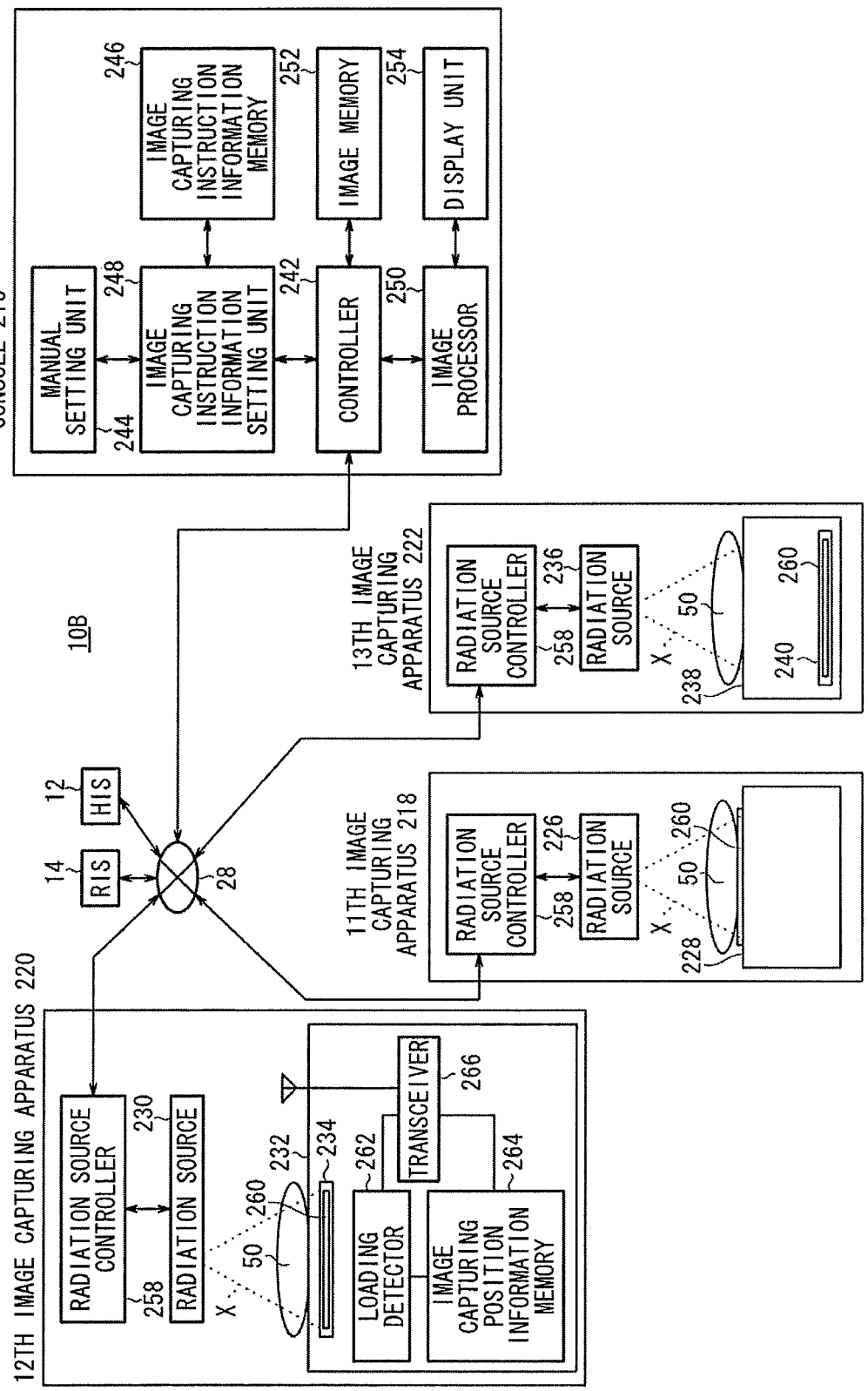
FIG. 13 is a block diagram of an assembly of a console, an eleventh image capturing apparatus, a twelfth image capturing apparatus, and a thirteenth image capturing apparatus of the second system.

FIG. 13 shows in block form an assembly of the console 216, the eleventh image capturing apparatus 218, the twelfth image capturing apparatus 220, and the thirteenth image capturing apparatus 222 of the second system 10B.

As shown in FIG. 13, the console 216 has a controller 242 which sends information to and receives information from the HIS 12, the RIS 14, the eleventh image capturing apparatus 218, the twelfth image capturing apparatus 220, and the thirteenth image capturing apparatus 222 through the in-house network 28.

The console 216 comprises a manual setting unit 244, an image capturing instruction information setting unit 248 for setting image capturing instruction information through the manual setting unit 244 or receiving image capturing instruction information set by the RIS 14 and storing the image capturing instruction information in an image capturing instruction information memory 246, an image processor 250 for performing an image processing process on radiation image information acquired from the eleventh image capturing apparatus 218, the twelfth image capturing apparatus 220, and the thirteenth image capturing apparatus 222, an image memory 252 for storing the processed radiation image information, and a display unit 254 for displaying the processed radiation image information.

The eleventh image capturing apparatus 218, which is a recumbent image capturing apparatus for capturing a radiation image of a subject 50, includes the radiation source 226 for being controlled by a radiation source controller 258, the image capturing base 228 disposed in confronting relation to the radiation source 226, and the electronic cassette 260 placed on the image capturing base 228.

The twelfth image capturing apparatus 220 includes the radiation source 230 for being controlled by a radiation source controller 258, the image capturing base 232 disposed in confronting relation to the radiation source 230, and the electronic cassette 260 loaded through the slot 234 into the image capturing base 232.

The image capturing base 232 comprises a loading detector (image capturing base positional information acquiring unit, image capturing base identifying unit) 262 for detecting a loaded state of the electronic cassette 260 in the slot 234 based on a signal sent from the electronic cassette 260, an image capturing position information memory (image capturing position information holding unit) 264 for storing image capturing position information required to adjust the magnification of radiation image information from the electronic cassette 260, e.g., the distance L11 from the upper surface of the image capturing base 232 to the image capturing surface of the electronic cassette 260, and a transceiver (signal transmitting/receiving unit) 266 for receiving a signal sent from the electronic cassette 260 to detect when the electronic cassette 260 is loaded through the slot 234 into the image capturing base 232, and sending the image capturing position information stored in the image capturing position information memory 264 to the electronic cassette 260 when the loading detector 262 detects the loading of the electronic cassette 260 into the image capturing base 232.

The thirteenth image capturing apparatus 222 includes the radiation source 236 for being controlled by a radiation source controller 258, the image capturing base 238 disposed in confronting relation to the radiation source 236, and the electronic cassette 260 loaded in the image capturing base 238 through the slot 240. The image capturing base 238 accommodates therein respective counterparts of the loading detector 262, the image capturing position information memory 264, and the transceiver 266 as in the image capturing base 232.

Figure 14:
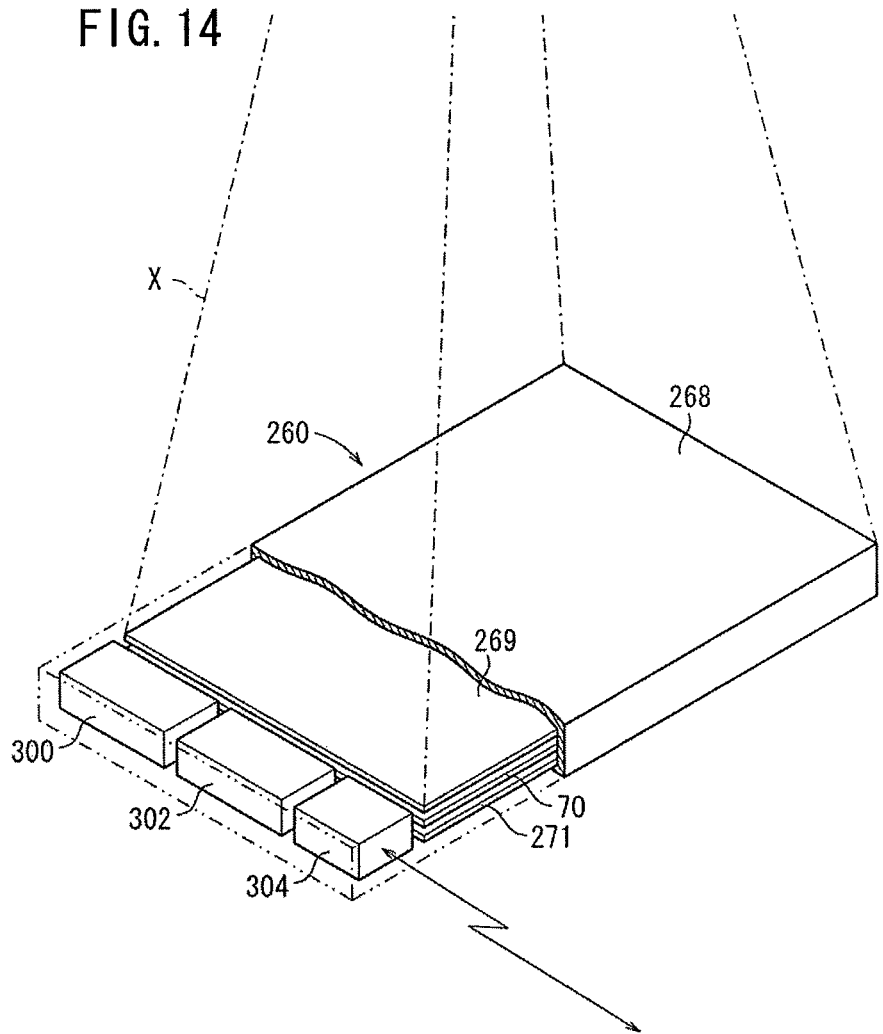
FIG. 14 is a perspective view, partly cut away, showing internal structural details of an electronic cassette.

FIG. 14 shows in perspective internal structural details of the electronic cassette 260. As shown in FIG. 14, the electronic cassette 260 has a casing 268 made of a material permeable to the radiation X. The casing 268 houses therein a grid 269 for removing scattered rays of the radiation X from the subject 50, the radiation detector 70 for detecting the radiation X that has passed through the subject 50, and a lead plate 271 for absorbing back scattered rays of the radiation X, which are successively arranged in the order from a surface of the casing 268 which is irradiated with the radiation X.

The casing 268 also houses therein a battery 300 as a power supply of the electronic cassette 260, a processor 302 energizing the radiation detector 70 with electric power supplied from the battery 300 and processing radiation image information, and a transceiver (signal transmitting/receiving unit) 304 for sending a signal indicative of the loading of the electronic cassette 260 through the slot 234 into the image capturing base 232 or through the slot 240 into the image capturing base 238, and receiving the image capturing position information stored in the image capturing position information memory 264 from the image capturing base 232 or 238.

Figure 15:
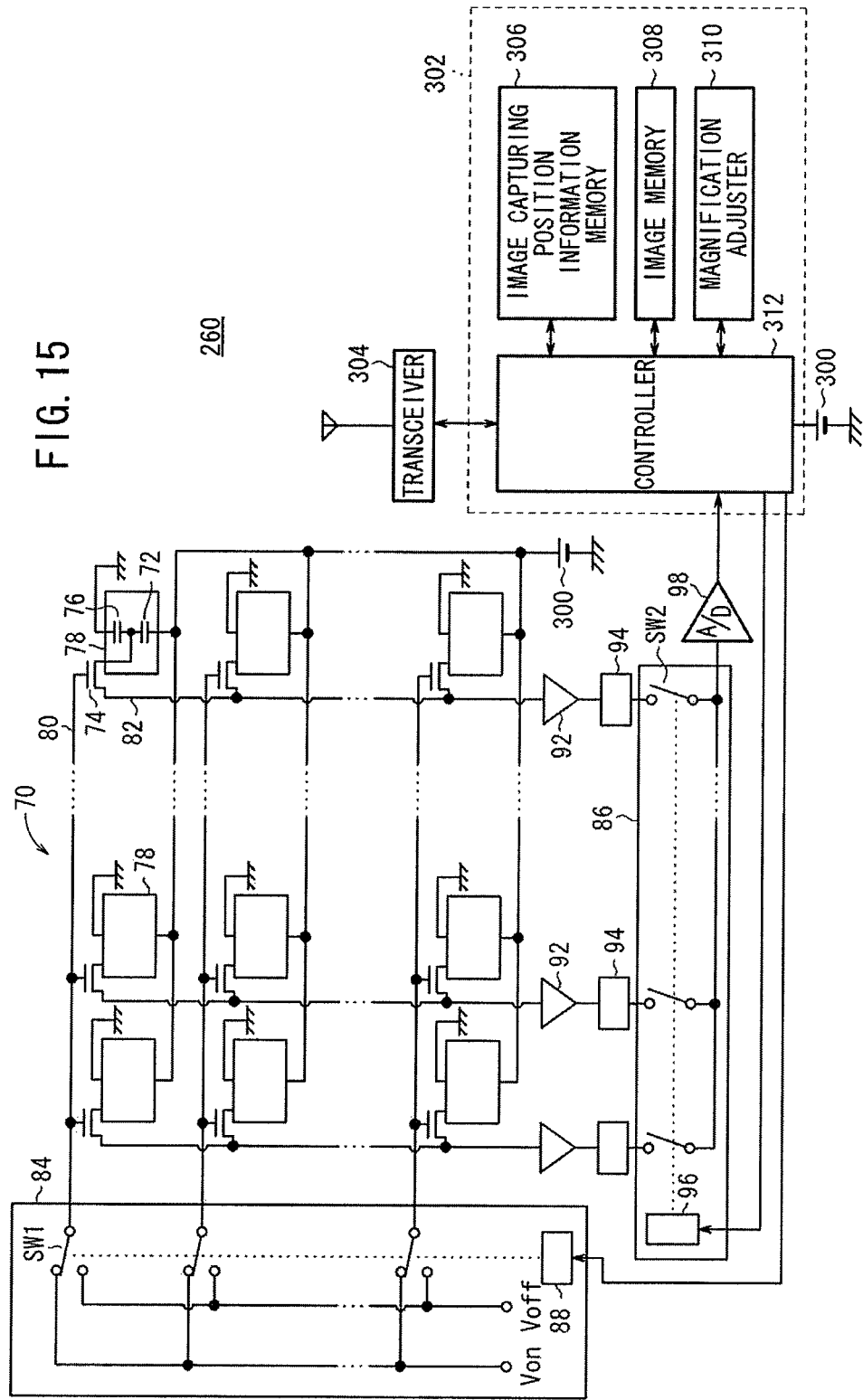
FIG. 15 is a block diagram of a circuit arrangement of a radiation detector in the electronic cassette.

FIG. 15 shows in block form a circuit arrangement of the radiation detector 70 to be loaded into the image capturing base 232 or 238 through the slot 234 or 240, and the processor 302.

The processor 302 comprises an image capturing position information memory (image capturing position information holding unit) 306 for storing image capturing position information received by a transceiver 304, an image memory 308 for storing captured radiation image information, a magnification adjuster 310 for adjusting the magnification of the radiation image information stored in the image memory 308 based on the image capturing position information stored in the image capturing position information memory 306, and a controller 312 for controlling the transceiver 304, the image capturing position information memory 306, the image memory 308, and the magnification adjuster 310, and also controlling a line scanning driver 84 and a multiplexer 86 to be described later. In order to prevent the processor 302 and the transceiver 304 from being damaged by the radiation X, a lead plate or the like should preferably be placed in the casing 268 near the surface thereof which is irradiated with the radiation X.

Details of the radiation detector 70 will not be described below as they are the same as those described above with reference to FIG. 4. The address decoder 88 and the address decoder 96 are supplied with respective address signals from the controller 312. A radiation image signal generated by the multiplexer 86 is converted by the A/D converter 98 into a digital image signal representing radiation image information, which is supplied to the controller 312. The controller 312 stores the radiation image information into the image memory 308 and supplies the radiation image information from the transceiver 304 through the in-house network 28 to the console 216.

An upstanding image capturing apparatus which may employ the radiation detector 70 or the stimulable phosphor panel P may be connected to the in-house network 28. Furthermore, image capturing apparatus of other specifications, such as a CT apparatus, an MR apparatus, etc. may also be connected to the in-house network 28, and consoles for controlling these image capturing apparatus may also be connected to the in-house network 28.

The second system 10B is basically constructed as described above. Operation of the second system 10B will be described below with reference to FIGS. 6, 16, and 17.

Figure 6:
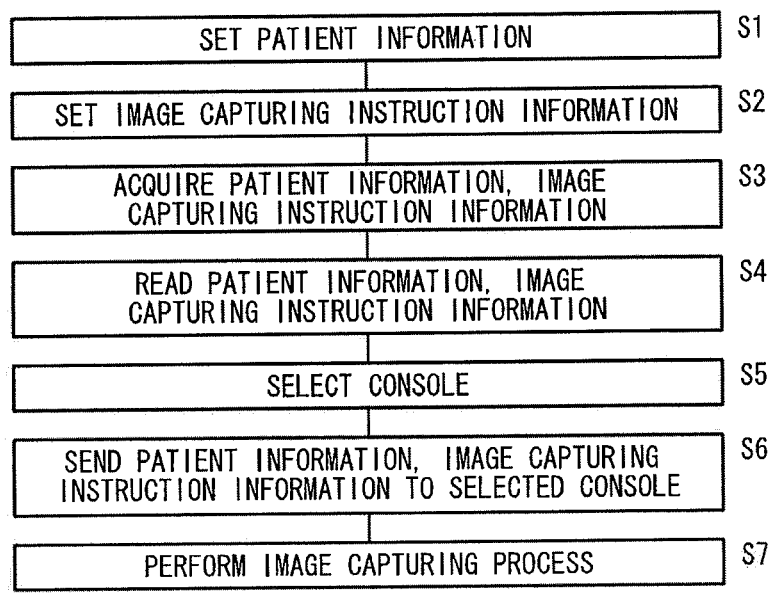
FIG. 6 is a flowchart of a general operating sequence of the first system.

First, the same process as the process shown in FIG. 6 is carried out (steps S1 through S4, step S7).

Specifically, patient information such as the name, gender, age, etc. of a patient is set using the HIS 12 (step S1 shown in FIG. 6), and image capturing instruction information such as a method of capturing a radiation image, a body region to be imaged, and an image capturing apparatus to be used to capture a radiation image, is set in relation to the patient information using the RIS 14 (step S2).

The controller 242 of the console 216 that is installed in the radiological department acquires the patient information and the image capturing instruction information from the RIS 14 via the in-house network 28 (step S3). The radiological technician sets and changes the image capturing instruction information using the manual setting unit 244 of the console 216. For example, the radiological technician changes from an image capturing apparatus set by the doctor using the RIS 14 to an image capturing apparatus suitable for a body region to be imaged and the condition of the patient. The image capturing instruction information setting unit 248 stores the patient information and the image capturing instruction information which have been acquired or the image capturing instruction information which has been changed or newly set into the image capturing instruction information memory 246.

Then, the image capturing instruction information setting unit 248 of the console 216 reads the patient information and the image capturing instruction information from the image capturing instruction information memory 246 (step S4). A process of capturing radiation image information is performed using the indicated image capturing apparatus according to the image capturing instruction information (step S7).

A process of capturing radiation image information of the subject 50 with the eleventh image capturing apparatus 218 controlled by the console 216 will be described below with reference to a flowchart of FIG. 16.

Figure 16:
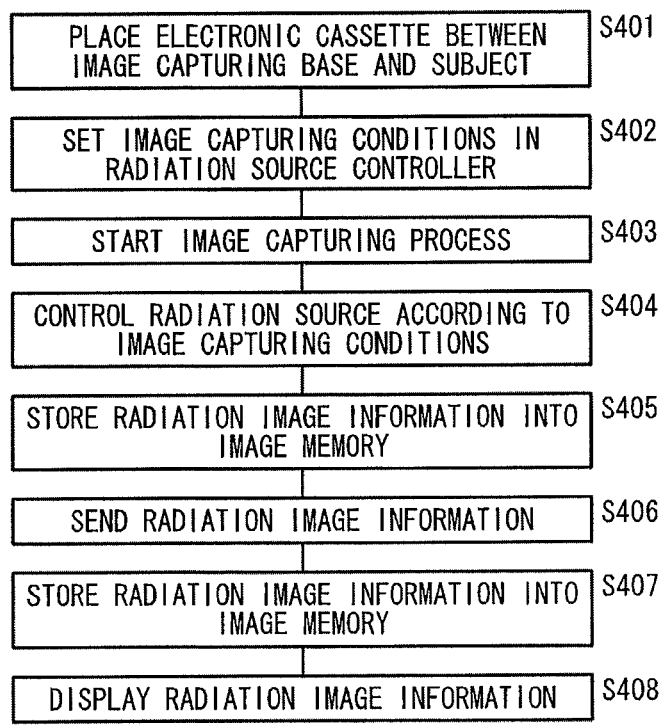
FIG. 16 is a flowchart of an operating sequence of the eleventh image capturing apparatus.

In the eleventh image capturing apparatus 218, the electronic cassette 260 is placed between the image capturing base 228 and the subject 50, and held in close contact with the subject 50 for capturing a radiation image thereof according to a contact image capturing process (step S401 in FIG. 16).

The console 216 sets image capturing conditions including a tube voltage, a tube current, and an irradiation time included in the image capturing instruction information in the radiation source controller 258 of the eleventh image capturing apparatus 218 (step S402).

After having positioned the subject 50 in a given position in the eleventh image capturing apparatus 218, the radiological technician operates an image capturing switch, not shown, to start an image capturing process (step S403). The radiation source controller 258 controls the radiation source 226 according to the set image capturing conditions (step S404) to apply the radiation X to the subject 50. The radiation X passes through the subject 50 and is applied to the radiation detector 70.

In the radiation detector 70, the electric charges stored in the storage capacitors 76 of the pixels 78 as radiation image information are read as an image signal through the signal lines 82 and supplied to the multiplexer 86. Based on the electric charges, the multiplexer 86 generates a radiation image signal, which is converted by the A/D converter 98 into a digital image signal representing radiation image information. The radiation image information is temporarily stored in the image memory 308 (step S405). Then, the radiation image information is sent from the transceiver 304 connected to the controller 312 to the console 216 (step S406).

In the console 216, the image processor 250 processes the radiation image information and stores the processed radiation image information into the image memory 252 (step S407). Then, the display unit 254 displays a radiation image based on the radiation image information (step S408). The radiological technician confirms the radiation image information displayed on the display unit 254 and determines whether another radiation image needs to be recaptured or not. If the radiological technician judges that the captured radiation image information is appropriate, then the radiation image information is sent through the in-house network 28 to the RIS 14 to be interpreted by the doctor for diagnosis.

A process of capturing radiation image information of the chest of the same subject 50 with the twelfth image capturing apparatus 220 controlled by the console 216 will be described below with reference to a flowchart of FIG. 17.

Figure 17:
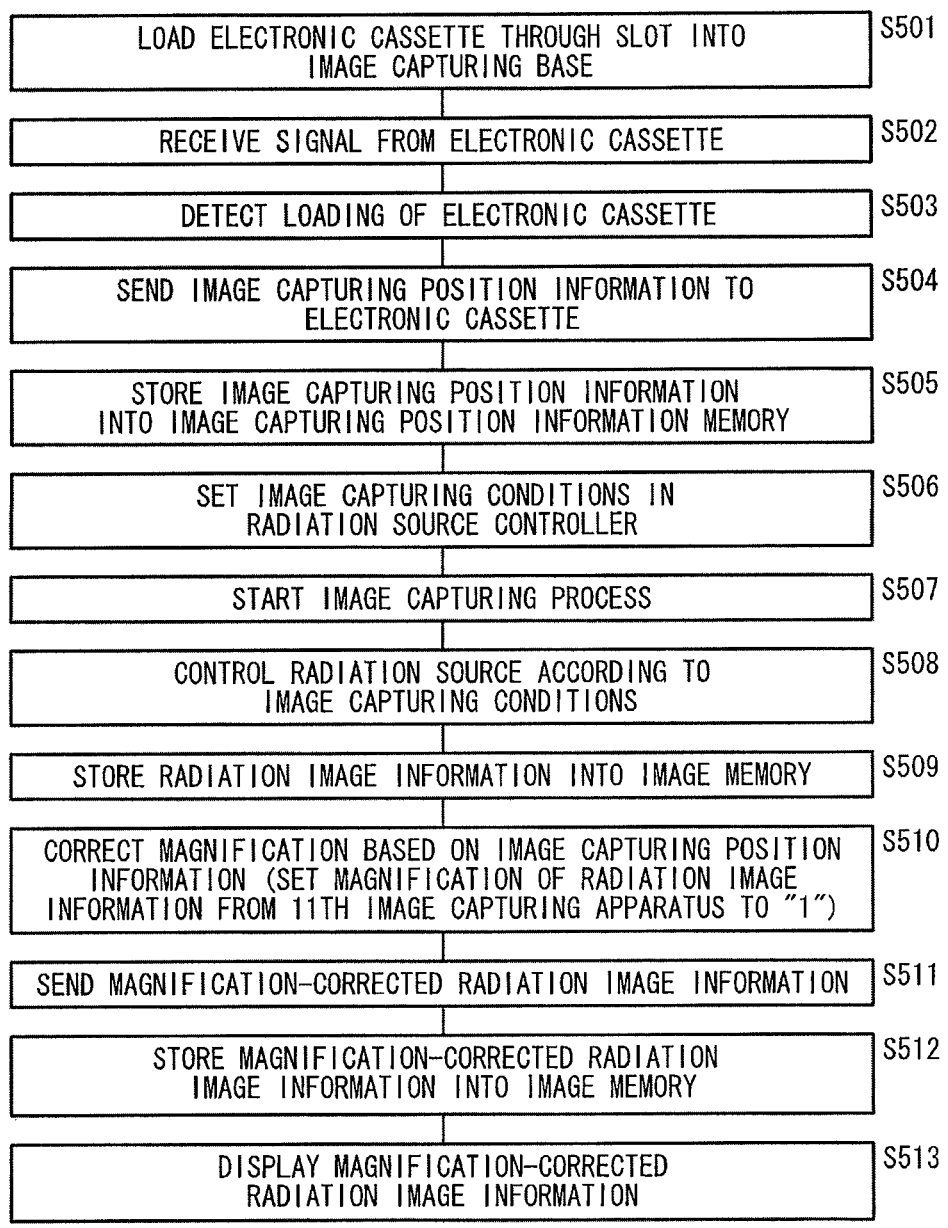
FIG. 17 is a flowchart of an operating sequence of the twelfth image capturing apparatus.

First, the electronic cassette 260 is loaded through the slot 234 into the image capturing base 232 (step S501 shown in FIG. 17). When the electronic cassette 260 is loaded, the transceiver 304 of the electronic cassette 260 generates a signal which is received by the transceiver 266 of the twelfth image capturing apparatus 220 (step S502). Based on the signal received by the transceiver 266, the loading detector 262 detects the loading of the electronic cassette 260 in the slot 234 of the image capturing base 232 (step S503). When the loading of the electronic cassette 260 is detected, the image capturing position information stored in the image capturing position information memory 264 is sent from the transceiver 266 to the electronic cassette 260 (step S504) and stored in the image capturing position information memory 306 (step S505).

Then, as with the contact image capturing process carried out by the eleventh image capturing apparatus 218, the console 216 sets image capturing conditions including a tube voltage, a tube current, and an irradiation time included in the image capturing instruction information in the radiation source controller 258 of the twelfth image capturing apparatus 220 (step S506). After having positioned the subject 50 in a given position in the twelfth image capturing apparatus 220, the radiological technician operates an image capturing switch, not shown, to start an image capturing process (step S507). The radiation source controller 258 controls the radiation source 230 according to the set image capturing conditions to apply the radiation X to the subject 50 (step S508). The radiation X passes through the subject 50 and is applied to the radiation detector 70.

The radiation detector 70 performs the same process as with the contact image capturing process carried out by the eleventh image capturing apparatus 218. The electric charges stored in the storage capacitors 76 of the pixels 78 are read as an image signal through the signal lines 82 and supplied to the multiplexer 86. Based on the electric charges, the multiplexer 86 generates a radiation image signal, which is converted by the A/D converter 98 into a digital image signal representing radiation image information. The controller 312 stores the radiation image information in the image memory 308 (step S509). In the processor 302, the magnification adjuster 310 calculates a magnification based on the image capturing position information stored in the image capturing position information memory 306, and adjusts the magnification of the radiation image information stored in the image memory 308 (step S510).

If the magnification of the radiation image information captured by the eleventh image capturing apparatus 218 is "1" and the radiation source 226 of the eleventh image capturing apparatus 218 and the electronic cassette 260 are spaced from each other by a distance L0, then the magnification of the radiation image information captured by the twelfth image capturing apparatus 220 is represented by (L0+L11)/L0. Therefore, the magnification adjuster 310 multiplies the radiation image information stored in the image memory 308 by L0/(L0+L11), and sends the magnification-adjusted radiation image information to the console 216 (step S511). In the console 216, the image processor 250 processes the radiation image information and stores the processed radiation image information into the image memory 252 (step S512).

If the image memory 252 stores the radiation image information which has been captured by the eleventh image capturing apparatus 218 according to the contact image capturing process and the radiation image information which has been captured by the twelfth image capturing apparatus 220, then the magnification of the radiation image information which has been captured by the twelfth image capturing apparatus 220 has been adjusted by the magnification adjuster 310 of the electronic cassette 260 such that its magnification is the same as the magnification of the radiation image information which has been captured by the eleventh image capturing apparatus 218. Therefore, even when a radiation image of the same subject 50 is captured by a different image capturing apparatus, it can be displayed on the display unit 254 at the same magnification as the magnification of the radiation image information which has been captured by the eleventh image capturing apparatus 218 according to the contact image capturing process (step S513).

When the thirteenth image capturing apparatus 222 captures radiation image information of the chest of the subject 50, it captures the radiation image information in the same manner as with the twelfth image capturing apparatus 220, and then the console 216 adjusts the magnification of the captured radiation image information, e.g., multiplies the captured radiation image information by L0/(L0+L12), and displays on the display unit 254 the magnification-adjusted radiation image information at the same magnification as the magnification of the radiation image information which has been captured by the eleventh image capturing apparatus 218 according to the contact image capturing process.

Figure 19:
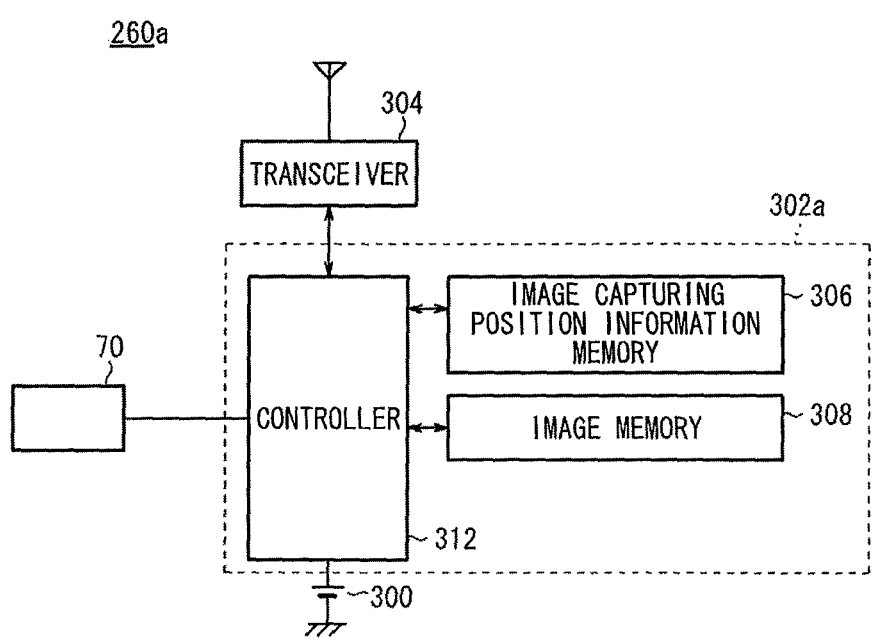
FIG. 19 is a block diagram of an electronic cassette for use with the third system.
Figure 20:
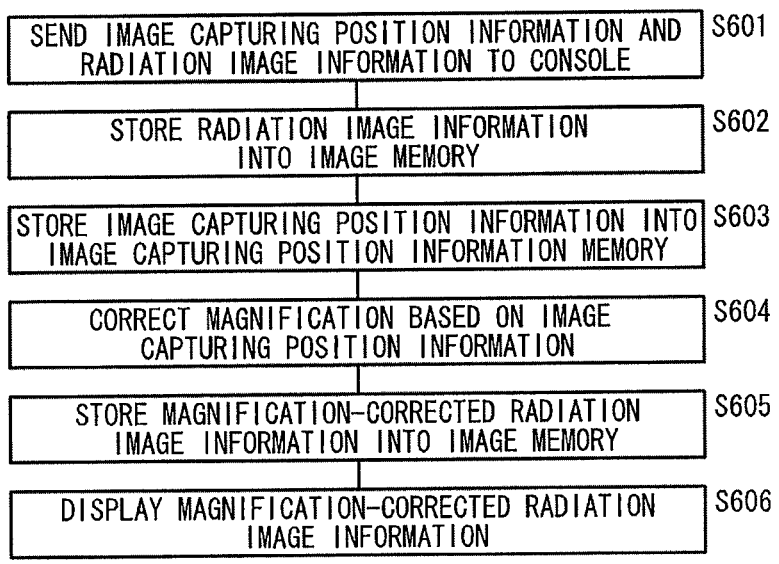
FIG. 20 is a flowchart of an operating sequence of a twelfth image capturing apparatus of the third system.

A radiation image capturing system 10C according to a third embodiment of the present invention (hereinafter referred to as "third system 10C") will be described below with reference to FIGS. 18 through 20.

Figure 18:
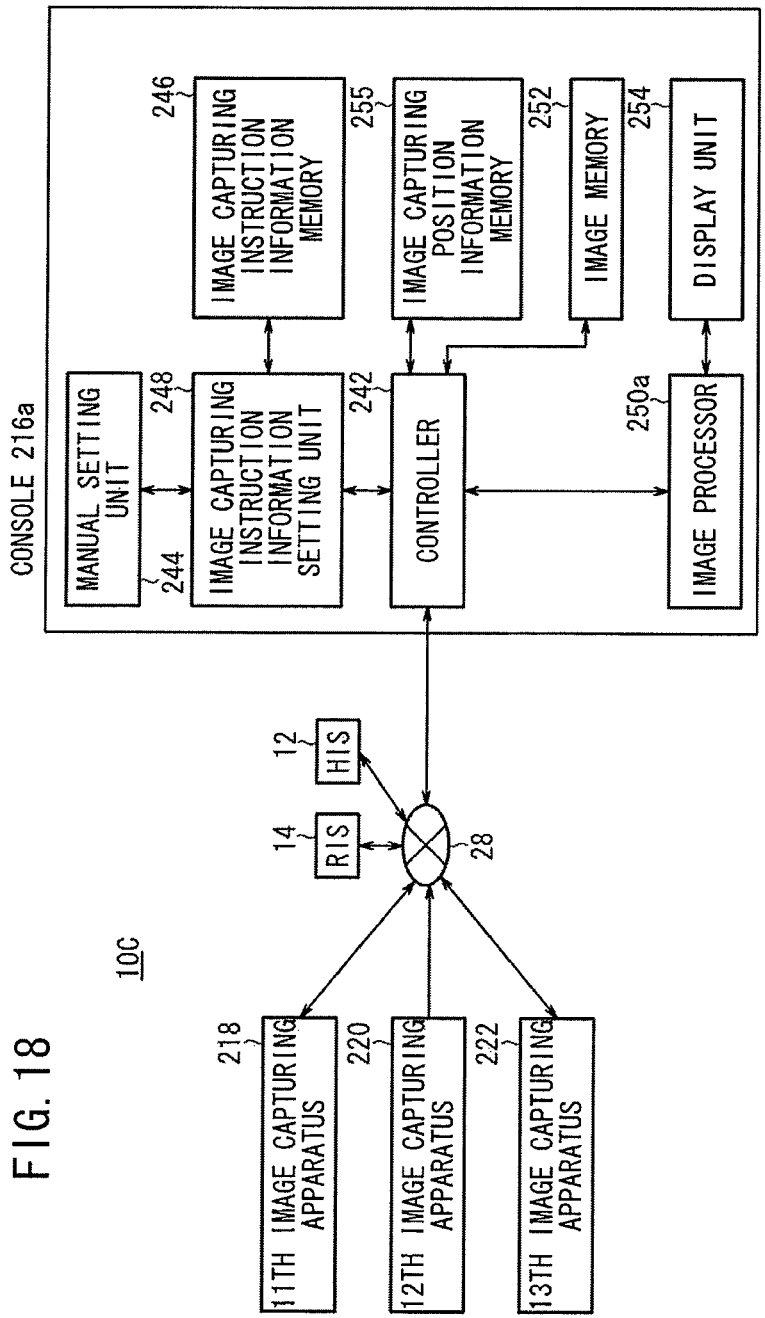
FIG. 18 is a block diagram of a third system according to the present invention.

As shown in FIG. 18, the third system 10C comprises, in addition to the HIS 12 and the RIS 14 referred to above, a console 216a, an eleventh image capturing apparatus 218, a twelfth image capturing apparatus 220, and a thirteenth image capturing apparatus 222 which are interconnected by the in-house network 28 in the hospital. If necessary, other consoles, other image capturing apparatus, and components may also be connected to the in-house network 28.

The console 216a includes the controller 242, the manual setting unit 244, the image capturing instruction information memory 246, the image capturing instruction information setting unit 248, the image memory 252, and the display unit 254, as described above with reference to FIG. 13. The console 216a also includes an image processor 250a for performing an image processing process including magnification correction on radiation image information acquired from the first to the thirteenth image capturing apparatus 218, 220, 222, and an image capturing position information memory 255 for storing image capturing position information used to calculate a magnification for adjusting the magnification of radiation image information. As shown in FIG. 19, an electronic cassette 260a has a processor 302a which includes the image capturing position information memory 306 and the image memory 308 of the processor 302 of the electronic cassette 260 shown in FIG. 15, but is devoid of the magnification adjuster 310.

A process of capturing radiation image information of the chest of the subject 50 with the twelfth image capturing apparatus 220 controlled by the console 216a, using the electronic cassette 260a, will be described below with reference to a flowchart of FIG. 20. Operation sequence details which are identical to those of the console 216 and the electronic cassette 260 will not be described below.

The electronic cassette 260a sends the image capturing position information of the twelfth image capturing apparatus 220 stored in the image capturing position information memory 306 and the radiation image information, whose magnification is not adjusted, stored in the image memory 308 to the console 216a (step S601).

The controller 242 of the console 216a. temporarily stores the radiation image information into the image memory 252 (step S602), and stores the image capturing position information into the image capturing position information memory 255 (step S603). The image processor 250a calculates a magnification (L0/(L0+L1)) based on the image capturing position information stored in the image capturing position information memory 255, adjusts the magnification of the radiation image information stored in the image memory 252 based on the calculated magnification (step S604), and stores the magnification-adjusted radiation image information into the image memory 252 (step S605). The radiation image information stored in the image memory 252 has been adjusted such that its magnification is the same as the magnification of the radiation image information which has been captured by the eleventh image capturing apparatus 218. If necessary, the display unit 254 displays a radiation image based on the radiation image information captured by the eleventh image capturing apparatus 218 and a radiation image based on the radiation image information captured by the twelfth image capturing apparatus 220 (step S606).

The image capturing position information stored in the image capturing position information memories 264 in the image capturing bases 232, 238 may be sent from the image capturing bases 232, 238 directly to the console 216a, not via the electronic cassettes 260, and may be stored into the image capturing position information memory 255. The image processor 250a may adjust the magnification of the radiation image information based on the image capturing position information stored in the image capturing position information memory 255.

Image capturing position information with respect to the image capturing bases 232, 238 may be stored in advance in the image capturing position information memory 255, and the magnification of the radiation image information may be adjusted based on the image capturing position information stored in the image capturing position information memory 255. Specifically, when the electronic cassette 260a is loaded through the slot 234 into the image capturing base 232, the image capturing position information memory 264 of the image capturing base 232 or the image capturing position information memory 306 of the electronic cassette 260a may send an identification code representing the image capturing base 232 to the console 216a. In the console 216a, the image processor 250a may identify the image capturing position information stored in the image capturing position information memory 255 based on the identification code, calculate a magnification based on the identified image capturing position information, and adjust the magnification of the radiation image information based on the calculated magnification.

Rather than acquiring image capturing position information from the image capturing position information memories 264 of the image capturing bases 232, 238, the radiological technician may specify an image capturing base from the console 216, or may specify an image capturing base based on the image capturing instruction information sent from the RIS 14 for identifying image capturing position information. In such a case, the twelfth image capturing apparatus 220 and the thirteenth image capturing apparatus 222 may be devoid of the loading detector 262, the image capturing position information memory 264, and the transceiver 266.

In the second system 10B and the third system 10C, each of the twelfth image capturing apparatus 220 and the thirteenth image capturing apparatus 222 have the loading detector 262 for detecting when the electronic cassette 260 is loaded. However, the processor 302 of the electronic cassette 260 may have the loading detector 262 for detecting when the electronic cassette 260 is loaded.

In the twelfth image capturing apparatus 220, the electronic cassette 260 may be placed between the image capturing base 232 and the subject 50, and held in close contact with the subject 50 for capturing a radiation image thereof according to the contact image capturing process, and a radiation image captured by the electronic cassette 260 loaded through the slot 234 into the image capturing base 232 of the twelfth image capturing apparatus 220 may be displayed at the same magnification as the magnification of the radiation image captured according to the contact image capturing process. In the contact image capturing process, the radiological technician operates the manual setting unit 244 to acquire the image capturing position information stored in the image capturing position information memory, and the radiation image is displayed at the same magnification based on the acquired image capturing position information. As with the twelfth image capturing apparatus 220, a radiation image captured by the thirteenth image capturing apparatus 222 according to the contact image capturing process and a radiation image captured by the electronic cassette 260 loaded through the slot 240 into the image capturing base 238 of the thirteenth image capturing apparatus 222 may be displayed at the same magnification.

The process of displaying a radiation image at the same magnification as the magnification of a radiation image captured by the eleventh image capturing apparatus 218 according to the contact image capturing process has been described above. However, radiation images captured respectively by the twelfth image capturing apparatus 220 and the thirteenth image capturing apparatus 222 may be displayed at the same magnification.

If the slot 234 in the image capturing base 232 of the twelfth image capturing apparatus 220 is combined with a mechanism for loading the electronic cassette 260 in different positions in the image capturing base 232, then radiation images may be captured at different magnifications by the twelfth image capturing apparatus 220. According to the present invention, those radiation images captured at different magnifications can be displayed at the same magnification.

In the radiation image capturing systems according to the illustrated embodiments, although certain preferred embodiments of the present invention have been shown and described in detail, it should be understood that various changes and modifications may be made therein without departing from the scope of the appended claims. The radiation detector 70 directly converts the applied radiation X into an electric signal with the photoelectric conversion layer 72 (direct conversion type). However, the radiation image capturing systems may employ a radiation detector including a scintillator for converting the applied radiation X into visible light and a solid-state detecting device such as of amorphous silicon (a-Si) or the like for converting the visible light into an electric signal (indirect conversion type: see Japanese Patent No. 3494683).

Alternatively, the radiation image capturing systems may employ a light readout type radiation detector for acquiring radiation image information. The light readout type radiation detector operates as follows: When a radiation is applied to a matrix of solid-state detecting devices, the solid-state detecting devices store an electrostatic latent image depending on the dose of the applied radiation. For reading the stored electrostatic latent image, reading light is applied to the radiation detector to generate an electric current representing radiation image information. After the radiation image information has been read, erasing light is applied to the radiation detector to erase radiation image information representing a residual electrostatic latent image from the radiation detector, which can thus be reused (see Japanese Laid-Open Patent Publication No. 2000-105297).

In the illustrated embodiments, the radiation detector 70 employs the TFTs 74. However, the TFTs 74 may be combined with other imaging devices such as a CMOS (Complementary Metal-Oxide Semiconductor) image sensor or a CCD (Charge-Coupled Device) image sensor which transfers electric charges while shifting them with shift pulses which correspond to the gate signals for the TFTs 74.

In the illustrated embodiments, the patient information is acquired through the HIS 12, and the image capturing instruction information is acquired through the RIS 14. However, the patient information and the image capturing instruction information may be directly entered using a keyboard, a coordinate input device, or the like which is connected to the host console or other consoles.

What is claimed is:

1. A radiation image capturing system comprising:
   a first image capturing apparatus for capturing a radiation image of a subject;
   a second image capturing apparatus for capturing a radiation image of the subject, the second image capturing apparatus having a specification different from that of the first image capturing apparatus;
   an image correcting device for correcting the radiation image of the subject which is captured by the second image capturing apparatus such that the radiation image of the subject which is captured by the second image capturing apparatus has the same magnification as that of the radiation image of the subject which is captured by the first image capturing apparatus; and
   a display unit for displaying the corrected radiation image,
   the first image capturing apparatus including a first radiation detector for detecting a radiation which has passed through the subject and converting the detected radiation into a radiation image, and
   the second image capturing apparatus including a second radiation detector for detecting a radiation which has passed through the subject and converting the detected radiation into a radiation image,
   wherein the image correcting device corrects the radiation image of the subject based on image capturing position information of the first image capturing apparatus with respect to the subject and image capturing position information of the second image capturing apparatus with respect to the subject,
   the image capturing position information of the first image capturing apparatus with respect to the subject represents a distance from an image capturing surface of the first image capturing apparatus to the first radiation detector, and
   the image capturing position information of the second image capturing apparatus with respect to the subject represents a distance from an image capturing surface of the second image capturing apparatus to the second radiation detector.

2. A method of capturing a radiation image with a radiation image capturing system including a first image capturing apparatus for capturing a radiation image of a subject, a second image capturing apparatus for capturing a radiation image of the subject, the second image capturing apparatus having a specification different from the first image capturing apparatus, and a display unit for displaying the radiation image, the first image capturing apparatus including a first radiation detector for detecting a radiation which has passed through the subject and converting the detected radiation into a radiation image, and the second image capturing apparatus including a second radiation detector for detecting a radiation which has passed through the subject and converting the detected radiation into a radiation image, the method comprising the steps of:
   acquiring a radiation image of the subject with the first image capturing apparatus;
   acquiring a radiation image of the subject with the second image capturing apparatus;
   correcting the radiation image of the subject which is captured by the second image capturing apparatus such that the radiation image of the subject which is captured by the second image capturing apparatus has the same magnification as that of the radiation image of the subject which is captured by the first image capturing apparatus; and
   displaying the corrected radiation image on the display unit,
   wherein correcting the radiation image comprises correcting the radiation image of the subject based on image capturing position information of the first image capturing apparatus with respect to the subject and image capturing position information of the second image capturing apparatus with respect to the subject,
   the image capturing position information of the first image capturing apparatus with respect to the subject represents a distance from an image capturing surface of the first image capturing apparatus to the first radiation detector, and
   the image capturing position information of the second image capturing apparatus with respect to the subject represents a distance from an image capturing surface of the second image capturing apparatus to the second radiation detector.

* * * * *